(12) United States Patent
Dahl et al.

(10) Patent No.: US 8,808,982 B2
(45) Date of Patent: Aug. 19, 2014

(54) COMPOSITIONS AND METHODS FOR REPROGRAMMING EUKARYOTIC CELLS

(75) Inventors: Gary Dahl, Madison, WI (US);
Anthony Person, Madison, WI (US);
Judith Meis, Fitchburg, WI (US);
Jerome Jendrisak, Madison, WI (US)

(73) Assignee: Cellscript, LLC, Madison, WI (US)

( * ) Notice: Subject to any disclaimer, the term of this patent is extended or adjusted under 35 U.S.C. 154(b) by 22 days.

(21) Appl. No.: 12/962,498

(22) Filed: Dec. 7, 2010

(65) Prior Publication Data

US 2011/0143436 A1 Jun. 16, 2011

Related U.S. Application Data

(60) Provisional application No. 61/267,312, filed on Dec. 7, 2009.

(51) Int. Cl.
*C12Q 1/68* (2006.01)
*C12N 5/071* (2010.01)
*C12N 15/87* (2006.01)

(52) U.S. Cl.
CPC .............. *C12N 15/87* (2013.01); *C12N 5/0696* (2013.01); *C12N 2501/604* (2013.01); *C12N 2501/608* (2013.01); *C12N 2501/602* (2013.01); *C12N 2501/606* (2013.01); *C12N 2501/605* (2013.01); *C12N 2501/603* (2013.01)
USPC ................................ 435/6; 435/325; 435/375

(58) Field of Classification Search
None
See application file for complete search history.

(56) References Cited

U.S. PATENT DOCUMENTS

| | | | |
|---|---|---|---|
| 5,824,497 A * | 10/1998 | Andrews et al. | 435/69.1 |
| 8,278,036 B2 | 10/2012 | Kariko et al. | |
| 2005/0137155 A1 | 6/2005 | McSwiggen et al. | |
| 2007/0087437 A1 | 4/2007 | Hu | |
| 2008/0293143 A1 | 11/2008 | Lin et al. | |
| 2009/0286852 A1 * | 11/2009 | Kariko et al. | 514/44 R |
| 2010/0167286 A1 * | 7/2010 | Reijo Pera et al. | 435/6 |
| 2012/0046346 A1 | 2/2012 | Rossi et al. | |
| 2012/0065252 A1 | 3/2012 | Schrum et al. | |
| 2012/0237978 A1 | 9/2012 | Kobilka et al. | |
| 2012/0251618 A1 | 10/2012 | Schrum et al. | |
| 2012/0322864 A1 | 12/2012 | Rossi et al. | |
| 2012/0322865 A1 | 12/2012 | Rossi et al. | |

FOREIGN PATENT DOCUMENTS

| | | |
|---|---|---|
| EP | 2072618 | 6/2009 |
| WO | 2008/151058 A2 | 12/2008 |
| WO | 2009/077134 A2 | 6/2009 |
| WO | 2009/101407 A2 | 8/2009 |
| WO | 2011/071931 | 6/2011 |
| WO | 2011/071936 | 6/2011 |
| WO | 2013/003475 | 1/2013 |

OTHER PUBLICATIONS

Gunnery et al. (Molecular and Cellular Biology 1995:3597-3607).*
Kim et al., 2008. Generation of human induced pluripotent stem cells by direct delivery of reprogramming proteins. Cell Stem Cell 4:472-476.
Warren et al. 2010. Highly Efficient Reprogramming to Pluripotency and Directed Differentiation of Human Cells with Synthetic Modified mRNA. Cell Stem Cell 7:1-13.
Treat et al., in Liposomes in the Therapy of Infectious Disease and Cancer, Lopez-Berestein and Fidler (eds.), Liss, New York, pp. 353-365 (1989).
Vierbuchen T et al. 2010. Direct conversion of fibroblasts to functional neurons by defined factors. Nature 463:1035-1041.
Weissman et al, 2000. HIV Gag mRNA Transfection of Dendritic Cells (DC) Delivers Encoded Antigen to MHC Class I and II Molecules, Causes DC Maturation, and Induces a Potent Human In Vitro Primary Immune Response. J Immunol 165:4710-4717.
Wilusz. 1988. A 64 kd nuclear protein binds to RNA segments that include the AAUAAA polyadenylation motif. Cell 52:221-228.
Xu et al. 2001. Feeder-free growth of undifferentiated human embryonic stem cells. Nat Biotechnol 19:971-974.
Yu et al, Sustained correction of B-cell development and function in a murine model of X-linked agammaglobulinemia (XLA) using retroviral-mediated gene transfer. Blood. 2004 104(5):1281-90.
Zelcer et al. 1981. The detection and characterization of viral-related double-stranded RNAs in tobacco mosaic virus-infected plants, Virology, 113(2):417-27.
Zimmerman et al. 2001. Electrolyte-and pH-stabilities of aqueous solid lipid nanoparticle (SLN) dispersions in artificial gastrointestinal media. Eur J Pharm Biopharm 52:203.
Zonta et al, Uretero-neocystostomy in a swine model of kidney transplantation: a new technique. J Surg Res. Apr. 2005;124(2):250-5.
Baker et al. 2005. RNA-Guided RNA modification: functional organization of the archeal H/ACA RNP. Genes & Dev. 19:1239-124.
Sousa et al. 2000. Use of T7 RNA Polymerase and Its Mutants for Incorporation of Nucleoside Analogs into RNA. Methods in Enzymology. 317:65-74.
Hancock. 1995. Reticulocyte Lysate Assay for In Vitro Translation and Posttranslational Modification of Ras Proteins. Methods in Enzymology. 255:60-.
Pradilla et al. 2004. Prevention of vasospasm following subarachnoid hemorrage in rabbits by anti-CD11/CD18 monoclonal antibody therapy. J Neurosurg. 101:88-92.

(Continued)

*Primary Examiner* — Kimberly Chong
(74) *Attorney, Agent, or Firm* — Casimir Jones, S.C.

(57) ABSTRACT

The present invention relates to methods for changing the state of differentiation of a eukaryotic cell, the methods comprising introducing mRNA encoding one or more reprogramming factors into a cell and maintaining the cell under conditions wherein the cell is viable and the mRNA that is introduced into the cell is expressed in sufficient amount and for sufficient time to generate a cell that exhibits a changed state of differentiation compared to the cell into which the mRNA was introduced, and compositions therefor. For example, the present invention provides mRNA molecules and methods for their use to reprogram human somatic cells into pluripotent stem cells.

26 Claims, 8 Drawing Sheets

(56) References Cited

OTHER PUBLICATIONS

Guo et al. 2000. Structure and function of a cap-independent translation element that functions in either the 3' or the 5' untranslated region. RNA. 6:1808-1820.

Koski et al. 2004. Cutting Edge: Innate Immune System Discriminates between RNA Containing Bacterial versus Eukaryotic Structural Features that Prime for High-Level IL-12 Secretion by Dendritic Cells. J Immunol. 127:3989-3993.

Desrosiers et al. 1974. Identification of Mehtylated Nucleosides in Messenger RNA from Novikoff Hepatoma Cells. PNAS. 71:3971-3975.

Gasche et al. 1999. Sequential Treatment of Anemia in Ulcerative Colitis with Intravenous Iron and Erythropletin. Digestion. 60:262-267.

International Search Report and Written Opinion for PCT/US2010/059317, mailed Aug. 22, 2011, issued by the ISA/KR.

International Search Report and Written Opinion for PCT/US2010/059305, mailed Aug. 23, 2011, issued by the ISA/KR.

Aasen et al. 2008. Efficient and rapid generation of induced pluripotent stem cells from human keratinocytes. Nature Biotech 26:1276-84.

Andrews-Pfannkoch et al. 2010. Hydroxyapatite-Mediated Separation of Double-Stranded DNA, Single-Stranded DNA, and RNA Genomes from Natural Viral Assemblages. Applied and Environmental Microbiology 76:5039-5045.

Abuchowski et al. 1981. Reduction of plasma urate levels in the cockerel with polyethylene glycol-uricase, J Pharmacol Exp Ther. 219:352-354.

Abuchowski et al. 1981. Immunosuppressive properties and circulating life of Achromobacter glutaminase-asparaginase covalently attached to polyethylene glycol in man, Cancer Treat Rep. 65:1077-81.

Barber. 1966. The chromatographic separation of ribonucleic acids. Biochem. Biophys. Acta 114:422-424.

Bernstein et al, Role for a bidentate ribonuclease in the initiation step of RNA interference. Nature 2001; 409(6818):363-6.

Bose, et al. 2004. Role of Nucleolin in Human Parainfluenza Virus Type 3 Infection of Human Lung Epithelial Cells. J. Virol. 78:8146-58.

Buccoliero et al, Elevation of lung surfactant phosphatidylcholine in mouse models of Sandhoff and of Niemann-Pick A disease. J Inherit Metab Dis 2004;27(5):641-8.

Caudy et al. 2002. Fragile X-related protein and VIG associate with the RNA interference machinery.Genes & Devel 16:2491-96.

Clawson and Smuckler. 1982. Increased Amounts of Double-Stranded RNA in the Cytoplasm of the Rat Liver following Treatment with Carcinogens. Cancer Research 42:3228-3231.

Copreni et al, Lentivirus-mediated gene transfer to the respiratory epithelium: a promising approach to gene therapy of cystic fibrosis. GeneTher 2004; 11 Suppl 1:867-75.

Dong Y et al. 2005. Poly(d,l-lactide-co-glycolide)/montmorillonite nanoparticles for oral delivery of anticancer drugs. Biomaterials 26:6068-76.

Easton et al. 2010. Rapid, nondenaturing RNA purification using weak anion-exchange fast performance liquid chromatography. RNA 16:647-653.

Edmonds. 1990. Polyadenylate polymerases. Methods Enzymol 181:161-170.

Faissner et al. 1982. Analysis of Poly peptides of the Tree Shrew (Tupaia) Herpesvirus by Gel Electrophoresis. J. Gen. Virol. 59:139-148.

Feng et al. 2008. PU.1 and C/EBPa/b convert fibroblasts into macrophage-like cells. Proc. Natl Acad. Sci. USA 105:6057-6062.

Franklin. 1966. Purification and Properties of the Replicative Intermediate of the RNA Bacteriophage R17. Proc. Natl. Acad. Sci. USA 55:1504-1511.

Gershon. 2000. (A)-tail of two polymerase structures. Nat Struct Biol 7:819-821.

Gjerde et al. 2009. RNA Purification and Analysis, Wiley-VCH Only TOC Provided. Will provide specific pages upon Examiner request.

Grentzmann et al, A dual-luciferase reporter system for studying recoding signals. RNA 1998;4(4):479-86.

Ieda et al. 2010. Direct reprogramming of fibroblasts into functional cardiomyocytes by defined factors. Cell 142:375-386.

Jiang, et al, Topical application of ketoconazole stimulates hair growth in C3H/HeN mice. J Dermatol 2005; 32(4):243-7.

Kariko et al, 1998, Phosphate-enhanced transfection of cationic lipid-complexed mRNA and plasmid DNA. Biochim Biophys Acta 1369:320-334.

Katre et al., 1987. Chemical modification of recombinant interleukin 2 by polyethylene glycol increases its potency in the murine Meth A sarcoma model. PNAS 84:1487-91.

Langer, New Methods of Drug Delivery. Science 249:1527-1533 (1990).

Lewandowski LJ et al. 1971. J. Virol. 8:809-812.

Lobenberg. et al. 1998. Improved body distribution of 14C-labelled AZT bound to nanoparticles in rats determined by radioluminography. J Drug Target 5:171.

Lopez-Berestien. 1989. Treatment of Systemic Fungal Infections with Liposomal-Amphotericin B, in Liposomes in the Therapy of Infectious Diseases and Cancer. Lopez-Erestein & Fidler eds. pp. 317-327.

McElwee et al, Transfer of CD8(+) cells induces localized hair loss whereas CD4(+)/CD25(−) cells promote systemic alopecia areata and CD4(+)/CD25(+) cells blockade disease onset in the C3H/HeJ mouse model. J Invest Dermatol 2005;124(5):947-57.

McGlynn et al, Differential subcellular localization of cholesterol, gangliosides, and glycosaminoglycans in murine models of mucopolysaccharide storage disorders. J Comp Neurol 2004 20;480(4):415-26.

Mackie. 1988. Vectors for the synthesis of specific RNAs in vitro. Biotechnology 10:253-267.

Martin et al. 1975. Purification of mRNA guanylyltransferase and mRNA (guanine-7-) methyltransferase from vaccinia virions. J Biol Chem 250:9322-9329.

Mellits et al. 1990. Removal of double-stranded contaminants from RNA transcripts: synthesis of adenovirus VA RNA1 from a T7 vector. Nucleic Acids Research 18:5401-5406.

Naz et al. 2002. Novel human prostate-specific cDNA: molecular cloning, expression, and immunobiology of the recombinant protein. Biochem Biophys Res Commun. 297:1075-84.

Nielsen PE. 1999. Peptide nucleic acids as therapeutic agents. Curr Opin Struct Biol 9:353-57.

Newmark et al. 1982. Preparation and Properties of Adducts of Streptokinase and Streptokinase-Plasmin Complex with Poly ethylene Glycol and Pluronic Polyol F38. J. Appl. Biochem. 4:185-189.

Ozawa et al. 2006. Amplification and analysis of cDNA generated from a single cell by 5'-RACE: application to isolation of antibody heavy and light chain variable gene sequences from single B cells. Biotechniques 40:469-470, 472, 474 passim.

Passini et al, AAV vector-mediated correction of brain pathology in a mouse model of Niemann-Pick A disease. Mol Ther 2005;11(5)754-62.

Pays. 1977. Characterization of Double-Stranded Ribonucleic Acid Sequences Present in the Intial Transcription Products of Rat Liver Chromatin. Biochem. J. 165:237-245.

Purchio et al. 1979. Methods for molecular cloning in eukaryotic cells. Methods in Enzymology. 68:357-375.

Racila et al. 2010. Transient expression of OCT 4 IS sufficient to allow human keratinocytes to change their differentiation pathway. Gene Therapy 18:294-303.

Sakuma et al. 1999. Mucoadhesion of polystyrene nanoparticles having surface hydrophilic polymeric chains in the gastrointestinal tract. Int J Pharm 177:161-72.

Sambrook and Russell, eds., Molecular Cloning, (2001) Only TOC Provided. Will provide specific pages upon Examiner Request.

Santini et al., 2000. Type I interferon as a powerful adjuvant for monocyte-derived dendritic cell development and activity in vitro and in Hu-PBL-SCID mice. J Exp Med 191:1777-178.

Satoh et al, X-linked immunodeficient mice spontaneously produce lupus-related anti-20 RNA helicase A autoantibodies, but are resistant to pristane-induced lupus. Int Immunol 2003, 15(9):1117-24.

(56) References Cited

OTHER PUBLICATIONS

Scholte et al. Animal models of cystic fibrosis. J Cyst Fibros 2004. 3 Suppl2:183-90.
Simonaro et al, Joint and bone disease in mucopolysaccharidoses VI and VII: identification of new therapeutic targets and biomarkers using animal models. Pediatr Res 2005;57(5 Pt 1):701-7.
Studier et al. 1986. Use of bacteriophage T7 RNA polymerase to direct selective high-level expression of cloned genes. J Mol Biol 189:113-130.
Szabo et al. 2010. Direct conversion of human fibroblasts to multilineage blood progenitors. Nature. 468:521-526.
Tanaka et al, Inhibition of heart transplant injury and graft coronary artery disease after prolonged organ ischemia by selective protein kinase C regulators. J Thorac Cardiovasc Surg 2005;129(5):1160-7.
Aoi et al. 2008. Generation of pluripotent stem cells from adult mouse liver and stomach cells. Science 321:699-702.
Banerjee. 1980. 5'-terminal cap structure in eucaryotic messenger ribonucleic acids. Microbiol Rev 44:175-205.
Chan et al. 2009. Live cell imaging distinguishes bona fide human iPS cells from partially reprogrammed cells. Nat Biotechnol 27:1033-1037.
Ebert et al. 2009. Induced pluripotent stem cells from a spinal muscular atrophy patient. Nature 457:277-280.
Gonzalez et al. 2009. Generation of mouse-induced pluripotent stem cells by transient expression of a single nonviral polycistronic vector. Proc Natl Acad Sci U S A 106:8918-8922.
Graf and Enver. 2009. Forcing cells to change lineages. Nature 462:587-594.
Grudzien et al. 2004. Novel cap analogs for in vitro synthesis of mRNAs with high translational efficiency. RNA 10:1479-1487.
Grudzien-Nogalska et al. 2007. Phosphorothioate cap analogs stabilize mRNA and increase translational efficiency in mammalian cells. RNA 13:1745-1755.
Higman et al. 1992. The *vaccinia virus* mRNA (guanine-N7-)-methyltransferase requires both subunits of the mRNA capping enzyme for activity. J Biol Chem 267:16430-16437.
Higman et al. 1994. The mRNA (guanine-7-)methyltransferase domain of the *vaccinia virus* mRNA capping enzyme. Expression in *Escherichia coli* and structural and kinetic comparison to the intact capping enzyme. J Biol Chem 269:14974-14981.
Huangfu et al. 2008. Induction of pluripotent stem cells from primary human fibroblasts with only Oct4 and Sox2. Nat Biotechnol 26:1269-1275.
Jemielity et al. 2003. Novel "anti-reverse" cap analogs with superior translational properties. RNA 9:1108-1122.
Kariko et al. 2008. Incorporation of pseudouridine into mRNA yields superior nonimmunogenic vector with increased translational capacity and biological stability. Mol Ther 16:1833-1840.
Kreig and Melton. 1984. Functional messenger RNAs are produced by SP6 in vitro transcription of cloned cDNAs. Nucleic Acid Res 12:7057-7070.
Lee et al. 2009. Modelling pathogenesis and treatment of familial dysautonomia using patient-specific iPSCs. Nature 461:402-406.
Maehr et al. 2009. Generation of pluripotent stem cells from patients with type 1 diabetes. Proc Natl Acad Sci U S A 106:15768-15773.
Myette and Niles. 1996. Domain structure of the *vaccinia virus* mRNA capping enzyme. Expression in *Escherichia coli* of a subdomain possessing the RNA 5'-triphosphatase and guanylyltransferase activities and a kinetic comparison to the full-size enzyme. J Biol Chem 271:11936-11944.
Nakagawa et al. 2008. Generation of induced pluripotent stem cells without Myc from mouse and human fibroblasts. Nat Biotechnol 26:101-106.
Okita et al. 2008. Generation of mouse induced pluripotent stem cells without viral vectors. Science 322:949-953.
Peng et al. 2002. Synthesis and application of a chain-terminating dinucleotide mRNA cap analog. Org Lett 4:161-164.
Shuman et al. 1980. Purification and characterization of a GTP-pyrophosphate exchange activity from vaccinia virions. Association of the GTP-pyrophosphate exchange activity with vaccinia mRNA guanylyltransferase. RNA (guanine-7-)methyltransferase complex (capping enzyme). J Biol Chem 255:11588-11598.
Shuman. 1995. Capping enzyme in eukaryotic mRNA synthesis. Prog Nucleic Acid Res Mol Biol 50:101-129.
Shuman. 2001. Structure, mechanism, and evolution of the mRNA capping apparatus. Prog Nucleic Acid Res Mol Biol 66:1-40.
Stadtfeld et al. 2008. Induced pluripotent stem cells generated without viral integration. Science 322:945-949.
Stepinski et al. 2001. Synthesis and properties of mRNAs containing the novel "anti-reverse" cap analogs 7-methyl (3'-O-methyl)GpppG and 7-methyl (3'-deoxy)GpppG. RNA 7:1486-1495.
Takahashi and Yamanaka. 2006. Induction of pluripotent stem cells from mouse embryonic and adult fibroblast cultures by defined factors. Cell 126:663-676.
Takahashi et al. 2007. Induction of pluripotent stem cells from adult human fibroblasts by defined factors. Cell 131:861-872.
Wang et al. 1997. Phylogeny of mRNA capping enzymes. Proc Nati Acad Sci U S A 94:9573-9578.
Woltjen et al. 2009. piggyBac transposition reprograms fibroblasts to induced pluripotent stem cells. Nature 458:766-770.
Yu et al. 2007. Induced pluripotent stem cell lines derived from human somatic cells. Science 318:1917-1920.
Yu et al. 2009. Human induced pluripotent stem cells free of vector and transgene sequences. Science 324:797-801.
Zhou et al. 2009. Generation of induced pluripotent stem cells using recombinant proteins. Cell Stem Cell 4:381-384.
Angel & Yanik. 2010. Innate Immune Suppression Enables Frequent Transfection with RNA Encoding Reprogramming Proteins. PLoS One 5(7):e11756, 7 pages.
Amarasinghe et al. 2001. *Escherichia coli* Ribonuclease III: Affinity Purification of Hexahistidine-Tagged Enzyme and Assays for Substrate Binding and Cleavage. Methods in Enzymology. Academic Press. 342:143-158.
Barkay. 1982. Processing of Bacteriophage T4 Primary Trascripts with Ribonuclease III. J Mol Virol 162:299-315.
Biocca et al. "Intracellular Expression of Anti-p21ras Single Chain Fv Fragments Inhibits Meiotic Maturation of *Xenopus* Oocytes." Biochemical and Biophysical Research Communications., 1993, 197:422-427.
Campbell et al. 2002. Pre-steady-state and Stopped-flow Fluorescence Analysis of *Escherichia coli* Ribonuclease III: Insights into Mechanism and Conformational Changes Associated with Binding and Catalysis. J Mol Biol 317:21-40.
Capoccia et al. "G-CSF and AMD3100 mobilize monocytes into the blood that stimulate angiogenesis in vivo through a paracrine mechanism," Blood. 2006. 108(7): 2438-2445.
Conrad & Rauhut. 2002. Ribonuclease III: new sense from nuisance. The International Joural of Biochemistry & Cell Biology 34:116-129.
Dunn. 1976. Rnase III Cleavage of Single-stranded RNA. J Biol Chem 251:3807-3814.
Dunn. 1982. Ribonuclease III. The Enzymes. Paul D. Boyer ed. Academic Press. pp. 485-499.
Epicentre Forum Publication, vol. 14-1 Published in Apr. 2007, 24 pages.
Kariko et al. 2011. Generating the optimal mRNA for therapy: HPLC purification eliminates immune activation and improves translation of nucleoside-modified, protein-encoding mRNA. Nucleic Acid Res 39:e142, 10 pages.
Kariko et al. 2012. Increased Erythropoiesis in Mice Injected with Submicrogram Quantities of Pseudouridine-containing mRNA Encoding Erythropoietin. Mol Ther 20:948-953.
Kormann et al. 2011. Expression of therapeutic proteins after delivery of chemically modified mRNA in mice. Nature Biotechnology 29:154-157.
Pe'ery et al. 1997. Synthesis and Purification of Single-=Stranded RNA for Use in Experiments with PKR and in Cell-Free Translation Systems. Methods: A companion to Methods in Enzymology, Academic Press Inc., New York, 11 (4):371-381.
Petit et al. "G-CSF Induces Stem Cell Mobilization by Decreasing Bone Marrow SDF-1 and Up-Regulating CXCR4," Nature Immunol., 2002, 3: 687-694.

(56) References Cited

OTHER PUBLICATIONS

Plews et al. 2010. Activation of pluripotency genes in human fibroblast cells by a novel mRNA based approach, PLoS One 5(12):e14397, 12 pages.

Robertson et al. 1968. Purification and Properties of Ribonuclease III from *Escherichia coli*. J Biol Chem 243:82-91.

Robertson. 1982. *Escherichia coli* Ribonuclease III Cleavage Sites. Cell 30:669-672.

Robertson et al. 1996. Paradoxical interactions between human delta hepatitis agent RNA and the cellular protein kinase PKR. Journal of Virology 70(8):5611-5617.

Rosa & Brivanlou. 2010. Synthetic mRNAs: Powerful Tools for Reprogramming and Differentiation of Human Cells. Cell Stem Cell 7:549-550.

Tavernier et al. 2012. Activation of pluripotency-associated genes in mouse embryonic fibroblasts by non-viral transfection with in vitro-derived mRNAs encoding Oct4, Sox2, Klf4 and cMyc. Biomaterials 33:412-417.

Virovic et al. 2005. Novel delivery methods for treatment of viral hepatitis: an update. Expert Opin Drug Deliv 2:707-17.

Yakubov et al. 2010. Reprogramming of human fibroblasts to pluripotent stem cells using mRNA of four transcription factors. Biochemical and Biophysical Research Communications 394:189-193.

Yang et al. 2002. Short RNA duplexes produced by hydrolysis with *Escherichia coli* Rnase III mediate effective RNA interference in mammalian cells. PNAS. 99:9942-9947.

International Search Report and Written Opinion for PCT/US2012/072301, mailed May 14, 2013, 33 pages.

\* cited by examiner

FIGURE 6

KLF4 mRNA cds (SEQ ID NO:1)

5' AUGAGGCAGCCACCUGGCGAGUCUGACAUGGCUGUCAGCGACGCGCUGCUCCCAUCUUUC
UCCACGUUCGCGUCUGGCCCGGCGGGAAGGGAGAAGACACUGCGUCAAGCAGGUGCCCCGAA
UAACCGCUGGCGGGAGGAGCUCUCCCACAUGAAGCGACUUCCCCCAGUGCUUCCCGGCCGCC
CCUAUGACCUGGCGGCGGCGACCGUGGCCACAGACCUGGAGAGCGGCGGAGCCGGUGCGGCU
UGCGGCGGUAGCAACCUGGCGCCCCUACCUCGGAGAGAGACCGAGGAGUUCAACGAUCUCCU
GGACCUGGACUUUAUUCUCUCCAAUUCGCUGACCCAUCCUCCGGAGUCAGUGGCCGCCACCG
UGUCCUCGUCAGCGUCAGCCUCCUCUUCGUCGUCGCCGUCGAGCAGCGGCCCUGCCAGCGCG
CCCUCCACCUGCAGCUUCACCUAUCCGAUCCGGGCCGGGAACGACCCGGGCGUGGCGCCGGG
CGGCACGGGCGGAGGCCUCCUCUAUGGCAGGGAGUCCGCUCCCCUCCGACGGCUCCCUUCA
ACCUGGCGGACAUCAACGACGUGAGCCCCUCGGGCGGCUUCGUGGCCGAGCUCCUGCGGCCA
GAAUUGGACCCGGUGUACAUUCCGCCGCAGCAGCCGCAGCCGCCAGGUGGCGGGCUGAUGGG
CAAGUUCGUGCUGAAGGCGUCGCUGAGCGCCCCUGGCAGCGAGUACGGCAGCCCGUCGGUCA
UCAGCGUCAGCAAAGGCAGCCCUGACGGCAGCCACCCGGUGGUGGUGGCGCCCUACAACGGC
GGGCCGCCGCGCACGUGCCCCAAGAUCAAGCAGGAGGCGGUCUCUUCGUGCACCCACUUGGG
CGCUGGACCCCCUCUCAGCAAUGGCCACCGGCCGGCUGCACACGACUUCCCCUGGGGCGGC
AGCUCCCCAGCAGGACUACCCCGACCCUGGGUCUUGAGGAAGUGCUGAGCAGCAGGGACUGU
CACCCUGCCCUGCCGCUUCCUCCCGGCUUCCAUCCCCACCCGGGGCCCAAUUACCCAUCCUU
CCUGCCCGAUCAGAUGCAGCCGCAAGUCCCGCCGCUCCAUUACCAAGAGCUCAUGCCACCCG
GUUCCUGCAUGCCAGAGGAGCCCAAGCCAAAGAGGGGAAGACGAUCGUGGCCCCGGAAAAGG
ACCGCCACCCACACUUGUGAUUACGCGGGCUGCGGCAAAACCUACACAAAGAGUUCCCAUCU
CAAGGCACACCUGCGAACCCACACAGGUGAGAAACCUUACCACUGUGACUGGGACGGCUGUG
GAUGGAAAUUCGCCCGCUCAGAUGAACUGACCAGGCACUACCGUAAACACACGGGGCACCGC
CCGUUCCAGUGCCAAAAAUGCGACCGAGCAUUUUCCAGGUCGGACCACCUCGCCUUACACAU
GAAGAGGCAUUUUUAA-3'

LIN28 mRNA cds (SEQ ID NO:2)

5' AUGGGCUCCGUGUCCAACCAGCAGUUUGCAGGUGGCUGCGCCAAGGCGGCAGAAGAGGCG
CCCGAGGAGGCGCCGGAGGACGCGGCCCGGGCGGCGGACGAGCCUCAGCUGCUGCACGGUGC
GGGCAUCUGUAAGUGGUUCAACGUGCGCAUGGGGUUCGGCUUCCUGUCCAUGACCGCCCGCG
CCGGGGUCGCGCUCGACCCCCAGUGGAUGUCUUUGUGCACCAGAGUAAGCUGCACAUGGAA
GGGUUCCGGAGCUUGAAGGAGGGUGAGGCAGUGGAGUUCACCUUUAAGAAGUCAGCCAAGGG
UCUGGAAUCCAUCCGUGUCACCGGACCUGGUGGAGUAUUCUGUAUUGGGAGUGAGAGGCGGC
CAAAAGGAAAGAGCAUGCAGAAGCGCAGAUCAAAAGGAGACAGGUGCUACAACUGUGGAGGU
CUAGAUCAUCAUGCCAAGGAAUGCAAGCUGCCACCCCAGCCCAAGAAGUGCCACUUCUGCCA
GAGCAUCAGCCAUAUGGUAGCCUCAUGUCCGCUGA-3'

FIGURE 7 cMYC mRNA cds (SEQ ID NO:3)

5AUGGAUUUUUUUCGGGUAGUGGAAAACCAGCAGCCUCCCGCGACGAUGCCCCUCAACGUUA
GCUUCACCAACAGGAACUAUGACCUCGACUACGACUCGGUGCAGCCGUAUUUCUACUGCGAC
GAGGAGGAGAACUUCUACCAGCAGCAGCAGCAGAGCGAGCUGCAGCCCCGGCGCCCAGCGA
GGAUAUCUGGAAGAAAUUCGAGCUGCUGCCCACCCCGCCCCUGUCCCCUAGCCGCCGCUCCG
GGCUCUGCUCGCCCUCCUACGUUGCGGUCACACCCUUCUCCCUUCGGGGAGACAACGACGGC
GGUGGCGGGAGCUUCUCCACGGCCGACCAGCUGGAGAUGGUGACCGAGCUGCUGGGAGGAGA
CAUGGUGAACCAGAGUUUCAUCUGCGACCCGGACGACGAGACCUUCAUCAAAAACAUCAUCA
UCCAGGACUGUAUGUGGAGCGGCUUCUCGGCCGCCGCCAAGCUCGUCUCAGAGAAGCUGGCC
UCCUACCAGGCUGCGCGCAAAGACAGCGGCAGCCCGAACCCCGCCCGCGGCCACAGCGUCUG
CUCCACCUCCAGCUUGUACCUGCAGGAUCUGAGCGCCGCCGCCUCAGAGUGCAUCGACCCCU
CGGUGGUCUUCCCCUACCCUCUCAACGACAGCAGCUCGCCCAAGUCCUGCGCCUCGCAAGAC
UCCAGCGCCUUCUCUCCGUCCUCGGAUUCUCUGCUCUCCUCGACGGAGUCCUCCCCGCAGGG
CAGCCCCGAGCCCCUGGUGCUCCAUGAGGAGACACCGCCCACCACCAGCAGCGACUCUGAGG
AGGAACAAGAAGAUGAGGAAGAAAUCGAUGUUGUUUCUGUGGAAAAGAGGCAGGCUCCUGGC
AAAAGGUCAGAGUCUGGAUCACCUUCUGCUGGAGGCCACAGCAAACCUCCUCACAGCCCACU
GGUCCUCAAGAGGUGCCACGUCUCCACACAUCAGCACAACUACGCAGCGCCUCCCUCCACUC
GGAAGGACUAUCCUGCUGCCAAGAGGGUCAAGUUGGACAGUGUCAGAGUCCUGAGACAGAUC
AGCAACAACCGAAAAUGCACCAGCCCCAGGUCCUCGGACACCGAGGAGAAUGUCAAGAGGCG
AACACACAACGUCUUGGAGCGCCAGAGGAGGAACGAGCUAAAACGGAGCUUUUUUGCCCUGC
GUGACCAGAUCCCGGAGUUGGAAAACAAUGAAAAGGCCCCCAAGGUAGUUAUCCUUAAAAAA
GCCACAGCAUACAUCCUGUCCGUCCAAGCAGAGGAGCAAAAGCUCAUUUCUGAAGAGGACUU
GUUGCGGAAACGACGAGAACAGUUGAAACACAAACUUGAACAGCUACGGAACUCUUGUGCGU
AA-3'

NANOG mRNA cds (SEQ ID NO:4)

5'-
AUGAGUGUGGAUCCAGCUUGUCCCCAAAGCUUGCCUUGCUUUGAAGCAUCCGACUGUAAAGA
AUCUUCACCUAUGCCUGUGAUUUGUGGGCCUGAAGAAAACUAUCCAUCCUUGCAAAUGUCUU
CUGCUGAGAUGCCUCACACAGAGACUGUCUCUCCUCUUCCUUCCUCCAUGGAUCUGCUUAUU
CAGGACAGCCCUGAUUCUUCCACCAGUCCCAAAGGCAAACAACCCACUUCUGCAGAGAAUAG
UGUCGCAAAAAAGGAAGACAAGGUCCCGGUCAAGAAACAGAAGACCAGAACUGUGUUCUCUU
CCACCCAGCUGUGUGUACUCAAUGAUAGAUUUCAGAGACAGAAAUACCUCAGCCUCCAGCAG
AUGCAAGAACUCUCCAACAUCCUGAACCUCAGCUACAAACAGGUGAAGACCUGGUUCCAGAA
CCAGAGAAUGAAAUCUAAGAGGUGGCAGAAAAACAACUGGCCGAAGAAUAGCAAUGGUGUGA
CGCAGAAGGCCUCAGCACCUACCUACCCCAGCCUCUACUCUUCCUACCACCAGGGAUGCCUG
GUGAACCCGACUGGGAACCUUCCAAUGUGGAGCAACCAGACCUGGAACAAUUCAACCUGGAG
CAACCAGACCCAGAACAUCCAGUCCUGGAGCAACCACUCCUGGAACACUCAGACCUGGUGCA
CCCAAUCCUGGAACAAUCAGGCCUGGAACAGUCCCUUCUAUAACUGUGGAGAGGAAUCUCUG
CAGUCCUGCAUGCACUUCCAGCCAAAUUCUCCUGCCAGUGACUUGGAGGCUGCCUUGGAAGC
UGCUGGGGAAGGCCUUAAUGUAAUACAGCAGACCACUAGGUAUUUUAGUACUCCACAAACCA
UGGAUUUAUUCCUAAACUACUCCAUGAACAUGCAACCUGAAGACGUGUGA-3'

FIGURE 8

OCT4 mRNA cds (SEQ ID NO:5)
5'-
AUGGCGGGACACCUGGCUUCAGAUUUUGCCUUCUCGCCCCCUCCAGGUGGUGGAGGUGAUGG
GCCAGGGGGGCCGGAGCCGGGCUGGGUUGAUCCUCGGACCUGGCUAAGCUUCCAAGGCCCUC
CUGGAGGGCCAGGAAUCGGGCCGGGGGUUGGGCCAGGCUCUGAGGUGUGGGGGAUUCCCCCA
UGCCCCCCGCCGUAUGAGUUCUGUGGGGGGAUGGCGUACUGUGGGCCCCAGGUUGGAGUGGG
GCUAGUGCCCCAAGGCGGCUUGGAGACCUCUCAGCCUGAGGGCGAAGCAGGAGUCGGGGUGG
AGAGCAACUCCGAUGGGGCCUCCCCGGAGCCCUGCACCGUCACCCCUGGUGCCGUGAAGCUG
GAGAAGGAGAAGCUGGAGCAAAACCCGGAGGAGUCCCAGGACAUCAAAGCUCUGCAGAAAGA
ACUCGAGCAAUUUGCCAAGCUCCUGAAGCAGAAGAGGAUCACCCUGGGAUAUACACAGGCCG
AUGUGGGGCUCACCCUGGGGGUUCUAUUUGGGAAGGUAUUCAGCCAAACGACCAUCUGCCGC
UUUGAGGCUCUGCAGCUUAGCUUCAAGAACAUGUGUAAGCUGCGGCCCUUGCUGCAGAAGUG
GGUGGAGGAAGCUGACAACAAUGAAAAUCUUCAGGAGAUAUGCAAAGCAGAAACCCUCGUGC
AGGCCCGAAAGAGAAAGCGAACCAGUAUCGAGAACCGAGUGAGAGGCAACCUGGAGAAUUUG
UUCCUGCAGUGCCCGAAACCCACACUGCAGCAGAUCAGCCACAUCGCCCAGCAGCUUGGGCU
CGAGAAGGAUGUGGUCCGAGUGUGGUUCUGUAACCGGCGCCAGAAGGGCAAGCGAUCAAGCA
GCGACUAUGCACAACGAGAGGAUUUUGAGGCUGCUGGGUCUCCUUUCUCAGGGGGACCAGUG
UCCUUUCCUCUGGCCCCAGGGCCCCAUUUUGGUACCCCAGGCUAUGGGAGCCCUCACUUCAC
UGCACUGUACUCCUCGGUCCCUUUCCCUGAGGGGGAAGCCUUUCCCCCUGUCUCUGUCACCA
CUCUGGGCUCUCCCAUGCAUUCAAACUGA-3'

SOX2 mRNA cds (SEQ ID NO:6)
5'-
AUGUACAACAUGAUGGAGACGGAGCUGAAGCCGCCGGGCCCGCAGCAAACUUCGGGGGGCGG
CGGCGGCAACUCCACCGCGGCGGCGGCCGGCGGCAACCAGAAAAACAGCCCGGACCGCGUCA
AGCGGCCCAUGAAUGCCUUCAUGGUGUGGUCCCGCGGGCAGCGGCGCAAGAUGGCCCAGGAG
AACCCCAAGAUGCACAACUCGGAGAUCAGCAAGCGCCUGGGCGCCGAGUGGAAACUUUUGUC
GGAGACGGAGAAGCGGCCGUUCAUCGACGAGGCUAAGCGGCUGCGAGCGCUGCACAUGAAGG
AGCACCCGGAUUAUAAAUACCGGCCCCGGCGGAAAACCAAGACGCUCAUGAAGAAGGAUAAG
UACACGCUGCCCGGCGGGCUGCUGGCCCCGGCGGCAAUAGCAUGGCGAGCGGGGUCGGGGU
GGGCGCCGGCCUGGGCGCGGGCGUGAACCAGCGCAUGGACAGUUACGCGCACAUGAACGGCU
GGAGCAACGGCAGCUACAGCAUGAUGCAGGACCAGCUGGGCUACCCGCAGCACCCGGGCCUC
AAUGCGCACGGCGCAGCGCAGAUGCAGCCCAUGCACCGCUACGACGUGAGCGCCCUGCAGUA
CAACUCCAUGACCAGCUCGCAGACCUACAUGAACGGCUCGCCCACCUACAGCAUGUCCUACU
CGCAGCAGGGCACCCCUGGCAUGGCUCUUGGCUCCAUGGGUUCGGUGGUCAAGUCCGAGGCC
AGCUCCAGCCCCCUGUGGUUACCUCUUCCUCCCACUCCAGGGCGCCCUGCCAGGCCGGGGA
CCUCCGGGACAUGAUCAGCAUGUAUCUCCCCGGCGCCGAGGUGCCGGAACCCGCCGCCCCA
GCAGACUUCACAUGUCCCAGCACUACCAGAGCGGCCCGGUGCCCGGCACGGCCAUUAACGGC
ACACUGCCCCUCUCACACAUGUGA-3'

SEQUENCE LISTING

```
<160> NUMBER OF SEQ ID NOS: 6

<210> SEQ ID NO 1
<211> LENGTH: 1440
<212> TYPE: RNA
<213> ORGANISM: Homo sapiens

<400> SEQUENCE: 1
augaggcagc caccuggcga gucugacaug gcugucagcg acgcgcugcu cccaucuuuc      60
uccacguucg cgucuggccc ggcgggaagg gagaagacac ugcgucaagc aggugcccg     120
```

```
aauaaccgcu ggcgggagga gcucuccac augaagcgac uucccccagu gcuuccggc      180
cgccccuaug accuggcggc ggcgaccgug gccacagacc uggagagcgg cggagccggu    240
gcggcuugcg gcgguagcaa ccuggcgccc cuaccucgga gagagaccga ggaguucaac    300
gaucuccugg accuggacuu uauucucucc aauucgcuga cccauccucc ggagucagug    360
gccgccaccg uguccucguc agcgucagcc uccucuucgu cgucgccguc gagcagcggc    420
ccugccagcg cgcccuccac cugcagcuuc accauccga uccgggccgg gaacgacccg     480
ggcguggcgc cgggcggcac gggcggaggc cuccucuaug gcagggaguc cgcuccccu     540
ccgacggcuc ccuucaaccu ggcggacauc aacgacguga gccccucggg cggcuucgug    600
gccgagcucc ugcggccaga auuggacccg uguacauuc cgccgcagca gccgcagccg     660
ccaggugcg ggcugauggg caaguucgug cugaaggcgu cgcugagcgc cccuggcagc     720
gaguacggca gcccgucggu caucagcguc agcaaaggca gcccugacgg cagccacccg    780
guggugugg cgcccuacaa cggcgggccc ccgcgcacgu gccccaagau caagcaggag     840
gcggucucuu cgugcaccca cuugggcgcu ggaccccuc ucagcaaugg ccaccggccg     900
gcugcacacg acuuccccu ggggcggcag cuccccagca ggacuacccc gacccugggu     960
cuugaggaag ugcugagcag cagggacugu cacccugccc ugccgcuucc ucccggcuuc   1020
caucccacc cggggcccaa uuacccaucc uuccugcccg aucagaugca gccgcaaguc    1080
ccgccgcucc auuaccaaga gcucaugcca cccgguccu gcaugccaga ggagcccaag    1140
ccaaagaggg gaagacgauc guggcccgg aaaaggaccg ccacccacac uugugauuac    1200
gcgggcugcg gcaaaaccua cacaaagagu ucccaucuca aggcacaccu gcgaacccac   1260
acaggugaga aaccuuacca cugugacugg gacggcugug gauggaaauu cgcccgcuca   1320
gaugaacuga ccaggcacua ccguaaacac acggggcacc gcccguucca ugccaaaaaa   1380
ugcgaccgag cauuuccag gucggaccac cucgccuuac acaugaagag gcauuuuuaa   1440
```

<210> SEQ ID NO 2
<211> LENGTH: 529
<212> TYPE: RNA
<213> ORGANISM: Homo sapiens

<400> SEQUENCE: 2

```
augggcuccg uguccaacca gcaguuugca gguggcugcg ccaaggcggc agaagaggcg     60
cccgaggagg cgccggagga cgcggcccgg gcggcggacg agccucagcu gcugcacggu    120
gcgggcaucu guaagugguu caacgucgcg auggggguucg gcuuccuguc caugaccgcc   180
cgcgccgggg ucgcgcucga ccccccagug gaugucuuug caccagag uaagcugcac     240
augaagggu uccggagcuu gaaggagggu gaggcagugg aguucaccuu uaagaaguca    300
gccaagggguc uggaauccau ccgugucacc ggaccugguu gaguauucug uauugggagu   360
gagaggcggc caaaaggaaa gagcaugcag aagcgcagau caaaaggaga caggugcuac   420
aacuguggag gucuagauca ucaugccaag gaaugcaagc ugccacccca gcccaagaag    480
ugccacuucu gccagagcau cagccauaug guagccucau guccgcuga                529
```

<210> SEQ ID NO 3
<211> LENGTH: 1365
<212> TYPE: RNA
<213> ORGANISM: Homo sapiens

<400> SEQUENCE: 3

```
auggauuuuu uucggguagu ggaaaaccag cagccucccg cgacgaugcc ccucaacguu    60
```

| | |
|---|---|
| agcuucacca acaggaacua ugaccucgac uacgacucgg ugcagccgua uuucuacugc | 120 |
| gacgaggagg agaacuucua ccagcagcag cagcagagcg agcugcagcc cccggcgccc | 180 |
| agcgaggaua ucuggaagaa auucgagcug cugcccaccc cgccccuguc cccuagccgc | 240 |
| cgcuccgggc ucugcucgcc cuccuacguu gcggucacac ccuucccccu ucggggagac | 300 |
| aacgacggcg guggcgggag cuucuccacg gccgaccagc uggagauggu gaccgagcug | 360 |
| cugggaggag acauggugaa ccagaguuuc aucugcgacc cggacgacga gaccuucauc | 420 |
| aaaaacauca ucauccagga cuguaugugg agcggcuucu cggccgccgc caagcucguc | 480 |
| ucagagaagc uggccuccua ccaggcugcg cgcaaagaca gcggcagccc gaaccccgcc | 540 |
| cgcggccaca gcgucugcuc caccuccagc uuguaccugc aggaucugag cgccgccgcc | 600 |
| ucagagugca cgaccccuc ggugucuuc cccuacccuc ucaacgacag cagcucgccc | 660 |
| aaguccugcg ccucgcaaga cuccagcgcc uucucuccgu ccucggauuc ucugcucucc | 720 |
| ucgacggagu ccucccccgca gggcagcccc gagccccugg ugcuccauga ggagacaccg | 780 |
| cccaccacca gcagcgacuc ugaggaggaa caagaagaug aggaagaaau cgauguuguu | 840 |
| ucuguggaaa agaggcaggc uccuggcaaa aggucagagu cuggaucacc uucgcuggga | 900 |
| ggccacagca aacuccuca cagcccacug guccucaaga ggugccacgu cuccacacau | 960 |
| cagcacaacu acgcagcgcc ucccuccacu cggaaggacu auccugcugc caagaggguc | 1020 |
| aaguuggaca gugucagagu ccugagacag aucagcaaca accgaaaaug caccagcccc | 1080 |
| agguccucgg acaccgagga gaaugucaag aggcgaacac acaacgucuu ggagcgccag | 1140 |
| aggaggaacg agcuaaaacg gagcuuuuuu gcccugcgug accagauccc ggaguuggaa | 1200 |
| aacaaugaaa aggcccccaa gguaguuauc cuuaaaaaag ccacagcaua caucucuguc | 1260 |
| guccaagcag aggagcaaaa gcucauuucu gaagaggacu uguugcggaa acgacgagaa | 1320 |
| caguugaaac acaaacuuga acagcuacgg aacucuugug cguaa | 1365 |

<210> SEQ ID NO 4
<211> LENGTH: 918
<212> TYPE: RNA
<213> ORGANISM: Homo sapiens

<400> SEQUENCE: 4

| | |
|---|---|
| augagugugg auccagccuug uccccaaagc uugccuugcu uugaagcauc cgacuguaaa | 60 |
| gaaucuucac cuaugccugu gauuugggg ccugaagaaa acuauccauc cuugcaaaug | 120 |
| ucuucugcug agaugccuca cacagagacu gucucuccuc uuccuuccuc cauggaucug | 180 |
| cuuauucagg acagcccuga uucuuccacc aguccccaaag gcaaacaacc cacuucugca | 240 |
| gagaauagug ucgcaaaaaa ggaagacaag guccgggucaa gaaacagaaa gaccagaacu | 300 |
| guguucucuu ccacccagcu guguguacuc aaugauagau ucagagacaa gaaauaccuc | 360 |
| agccuccagc agaugcaaga acucuccaac auccugaacc ucagcuacaa acaggugaag | 420 |
| accugguucc agaaccagag aaugaaaucu aagaggguggc agaaaaacaa cuggccgaag | 480 |
| aauagcaaug ugugacgca gaaggccuca gcaccuaccu accccagccu cuacucuucc | 540 |
| uaccaccagg gaugccuggu gaacccgacu gggaaccuuc caauggagc aaccagaccc | 600 |
| uggaacaauu caaccuggag caaccagacc cagaacaucc aguccuggag caaccacucc | 660 |
| uggaacacuc agaccuggug cacccaauc uggaacaauc aggccuggaa caguccuuc | 720 |
| uauaacugug gagaggaauc ucugcagucc ugcaugcacu uccagccaaa uucuccugcc | 780 |

| | |
|---|---:|
| agugacuugg aggcugccuu ggaagcugcu ggggaaggcc uuaauguaau acagcagacc | 840 |
| acuagguauu uuaguacucc acaaaccaug gauuuauucc uaaacuacuc caugaacaug | 900 |
| caaccugaag acguguga | 918 |

<210> SEQ ID NO 5
<211> LENGTH: 1083
<212> TYPE: RNA
<213> ORGANISM: Homo sapiens

<400> SEQUENCE: 5

| | |
|---|---:|
| auggcgggac accuggcuuc agauuuugcc uucucgcccc cuccaggugg uggaggugau | 60 |
| gggccagggg ggccggagcc gggcuggguu gauccucgga ccuggcuaag cuuccaaggc | 120 |
| ccuccuggag ggccaggaau cgggccgggg guugggccag gcucgaggu gugggggauu | 180 |
| cccccaugcc ccccgccgua ugaguucugu gggggaugg cguacugugg ccccagguu | 240 |
| ggagugggc uagugcccca aggcgguuu gagaccucuc agccugaggg cgaagcagga | 300 |
| gucgggugg agagcaacuc cgaugggcc uccccggagc ccugcaccgu caccccuggu | 360 |
| gccgugaagc uggagaagga gaagcuggag caaaacccgg aggagucca ggacaucaaa | 420 |
| gcucugcaga agaacucga gcaauuugcc aagcuccuga gcagaagag gaucacccug | 480 |
| ggauauacac aggccgaugu ggggcucacc cuggggguuc uauuuggga gguauucagc | 540 |
| caaacgacca ucugccgcuu ugaggcucug cagcuuagcu ucaagaacau guguaagcug | 600 |
| cggcccuugc ugcagaagug gguggaggaa gcugacaaca augaaaaucu ucaggagaua | 660 |
| ugcaaagcag aaacccucgu gcaggcccga aagagaaagc gaaccaguau cgagaaccga | 720 |
| gugagaggca accuggagaa uuuguuccug cagugcccga aacccacacu gcagcagauc | 780 |
| agccacaucg cccagcagcu uggggcucgag aaggaugugg uccgagugug guucuguaac | 840 |
| cggcgccaga agggcaagcg aucaagcagc gacuaugcac aacgagagga uuugaggcu | 900 |
| gcugggucuc cuuucucagg gggaccagug uccuuuccuc uggccccagg gccccauuuu | 960 |
| gguaccccag gcuauggagg cccucacuuc acugcacugu acuccucggu cccuuucccu | 1020 |
| gagggggaag ccuuucccc ugucucuguc accacucugg gcucucccau gcauucaaac | 1080 |
| uga | 1083 |

<210> SEQ ID NO 6
<211> LENGTH: 954
<212> TYPE: RNA
<213> ORGANISM: Homo sapiens

<400> SEQUENCE: 6

| | |
|---|---:|
| auguacaaca ugauggagac ggagcugaag ccgccgggcc cgcagcaaac uucggggggc | 60 |
| ggcggcggca acuccaccgc ggcggcggcc ggcggcaacc agaaaaacag cccggaccgc | 120 |
| gucaagcggc ccaugaaugc cuucauggug uggcccgcg ggcagcggcg caagaugggcc | 180 |
| caggagaacc ccaagaugca caacucggag aucagcaagc gccugggcgc cgagugggaaa | 240 |
| cuuuugucgg agacggagaa gcggccguuc aucgacgagg cuaagcggcu gcgagcgcug | 300 |
| cacaugaagg agcaccccgga uuauaaauac cggccccggc ggaaaaccaa gacgcucaug | 360 |
| aagaaggaua aguacacgcu gccggcgggg cugcuggccc ccgcggcaa uagcauggcg | 420 |
| agcggggucg ggugggcgc cggccuggcc gcggcguga ccagcgcau ggacaguuac | 480 |
| gcgcacauga acggcuggag caacggcagc uacagcauga ugcaggacca gcugggcuac | 540 |
| ccgcagcacc cgggccucaa ugcgcacggc gcagcgcaga ugcagcccau gcaccgcuac | 600 |

```
gacgugagcg cccugcagua caacuccaug accagcucgc agaccuacau gaacggcucg    660
cccaccuaca gcauguccua cucgcagcag ggcaccccug gcauggcucu uggcuccaug    720
gguucggugg ucaaguccga ggccagcucc agccccccug ugguuaccuc uuccucccac    780
uccagggcgc ccugccaggc cggggaccuc cgggacauga ucagcaugua ucuccccggc    840
gccgaggugc cggaacccgc cgcccccagc agacuucaca ugucccagca cuaccagagc    900
ggcccggugc ccggcacggc cauuaacggc acacugcccc ucucacacau guga          954
```

COMPOSITIONS AND METHODS FOR REPROGRAMMING EUKARYOTIC CELLS

The present application claims priority to U.S. Provisional Application Ser. No. 61/267,312 filed Dec. 7, 2009, which is herein incorporated by reference in its entirety.

FIELD OF THE INVENTION

The present invention relates to compositions and rapid, efficient methods for changing the state of differentiation of a eukaryotic cell. For example, the present invention provides mRNA molecules and methods for their use to reprogram cells, such as to reprogram human somatic cells to pluripotent stem cells.

BACKGROUND

In 2006, it was reported (Takahashi and Yamanaka 2006) that the introduction of genes encoding four protein factors (OCT4 (Octamer-4; POU class 5 homeobox 1), SOX2 (SRY (sex determining region Y)-box 2), KLF4 (Krueppel-like factor 4), and c-MYC) into differentiated mouse somatic cells induced those cells to become pluripotent stem cells, (referred to herein as "induced pluripotent stem cells," "iPS cells," or "iPSCs"). Following this original report, pluripotent stem cells were also induced by transforming human somatic cells with genes encoding the similar human protein factors (OCT4, SOX2, KLF4, and c-MYC) (Takahashi et al. 2007), or by transforming human somatic cells with genes encoding human OCT4 and SOX2 factors plus genes encoding two other human factors, NANOG and LIN28 (Lin-28 homolog A) (Yu et al. 2007). All of these methods used retroviruses or lentiviruses to integrate genes encoding the reprogramming factors into the genomes of the transformed cells and the somatic cells were reprogrammed into iPS cells only over a long period of time (e.g., in excess of a week).

The generation iPS cells from differentiated somatic cells offers great promise as a possible means for treating diseases through cell transplantation. The possibility to generate iPS cells from somatic cells from individual patients also may enable development of patient-specific therapies with less risk due to immune rejection. Still further, generation of iPS cells from disease-specific somatic cells offers promise as a means to study and develop drugs to treat specific disease states (Ebert et al. 2009, Lee et al. 2009, Maehr et al. 2009).

Viral delivery of genes encoding protein reprogramming factors (or "iPSC factors") provides a highly efficient way to make iPS cells from somatic cells, but the integration of exogenous DNA into the genome, whether random or non-random, creates unpredictable outcomes and can ultimately lead to cancer (Nakagawa et al. 2008). New reports show that iPS cells can be created (at lower efficiency) by using other methods that do not require genome integration. For example, repeated transfections of expression plasmids containing genes for OCT4, SOX2, KLF4 and c-MYC into mouse embryonic fibroblasts to generate iPS cells was demonstrated (Okita et al. 2008). Induced pluripotent stem cells were also generated from human somatic cells by introduction of a plasmid that expressed genes encoding human OCT4, SOX2, c-MYC, KLF4, NANOG and LIN28 (Yu et al. 2009). Other successful approaches for generating iPS cells include treating somatic cells with: recombinant protein reprogramming factors (Zhou et al. 2009); non-integrating adenoviruses (Stadtfeld et al. 2008); or piggyBac transposons (Woltjen et al. 2009) to deliver reprogramming factors. Presently, the generation of iPS cells using these non-viral delivery techniques to deliver reprogramming factors is extremely inefficient. Future methods for generating iPS cells for potential clinical applications will need to increase the speed and efficiency of iPS cell formation while maintaining genome integrity.

SUMMARY OF THE INVENTION

The present invention relates to compositions and rapid, efficient methods for changing the state of differentiation of a eukaryotic cell. For example, the present invention provides mRNA molecules and methods for their use to reprogram cells, such as to reprogram human somatic cells to pluripotent stem cells.

In some embodiments, the present invention provides methods for changing the state of differentiation of a cell comprising: introducing an mRNA encoding an iPS cell induction factor into a somatic cell to generate a reprogrammed cell. In certain embodiments, the introducing comprises delivering the mRNA to the somatic cell with a transfection reagent. In other embodiments, the reprogrammed cell is a dedifferentiated cell. In further embodiments, the reprogrammed cell is a transdifferentiated cell.

In particular embodiments, the mRNA is polyadenylated. In other embodiments, the mRNA comprises a poly-A tail 100-200 nucleotides in length. In further embodiments, the mRNA comprises capped mRNA. In certain embodiments, the mRNA is a population of mRNA molecules, the population having greater than 99% capped mRNA. In additional embodiments, the mRNA comprises pseudouridine in place of uridine. In other embodiments, the iPS cell induction factor is selected from the group consisting of KLF4, LIN28, c-MYC, NANOG, OCT4, and SOX2. In particular embodiments, the introducing comprises introducing mRNA encoding a plurality of iPS cell induction factors into the somatic cell. In further embodiments, the plurality of iPS cell induction factors comprises each of KLF4, LIN28, c-MYC, NANOG, OCT4, and SOX2. In additional embodiments, the cell is a fibroblast. In other embodiments, the reprogrammed cell is a pluripotent stem cell. In other embodiments, the dedifferentiated cell expresses NANOG and TRA-1-60. In further embodiments, the cell is in vitro. In additional embodiments, the cell resides in culture. In particular embodiments, the cells reside in MEF-conditioned medium.

In certain embodiments, the present invention provides compositions comprising an mRNA encoding an iPS cell induction factor, the mRNA having pseudouridine in place of uridine. In other embodiments, the composition comprises mRNA encoding a plurality of iPS cell induction factors, selected from the group consisting of KLF4, LIN28, c-MYC, NANOG, OCT4, and SOX2. In further embodiments, the plurality comprises three or more, or four or more, or five or more, or six.

In certain embodiments, the compositions described above are packaged in a kit. In some embodiments, the compositions comprise a transfection reagent and an mRNA encoding an iPS cell induction factor.

DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

FIG. 2 shows phase contrast images of an iPS cell colony at 12 days after the final transfection with mRNA encoding reprogramming factors (A, C). NANOG staining (green) is observed in colony #1 (B, D). Images A and B are at 10× magnification. C and D are at 20× magnification.

FIG. 3 shows phase contrast images of iPS colonies derived from 1079 cells (A, D) and IMR90 cells (G). The same iPS colony shown in (A) is positive for both NANOG (B) and TRA-1-60 (C). The iPS colony shown in (D) is NANOG-positive (E) and TRA-1-60-positive (F). The iPS colony generated from IMR90 fibroblasts (G) is also positive for both NANOG (H) and TRA-1-60 (I). All images are at 20× magnification.

FIG. 6 provides the mRNA coding sequence for KLF4 (SEQ ID NO:1) and LIN28 (SEQ ID NO:2).

FIG. 7 provides the mRNA coding sequence for cMYC (SEQ ID NO:3) and NANOG (SEQ ID NO:4).

FIG. 8 provides the mRNA coding sequence for OCT4 (SEQ ID NO:5) and SOX2 (SEQ ID NO:6).

DEFINITIONS

Figure 1:
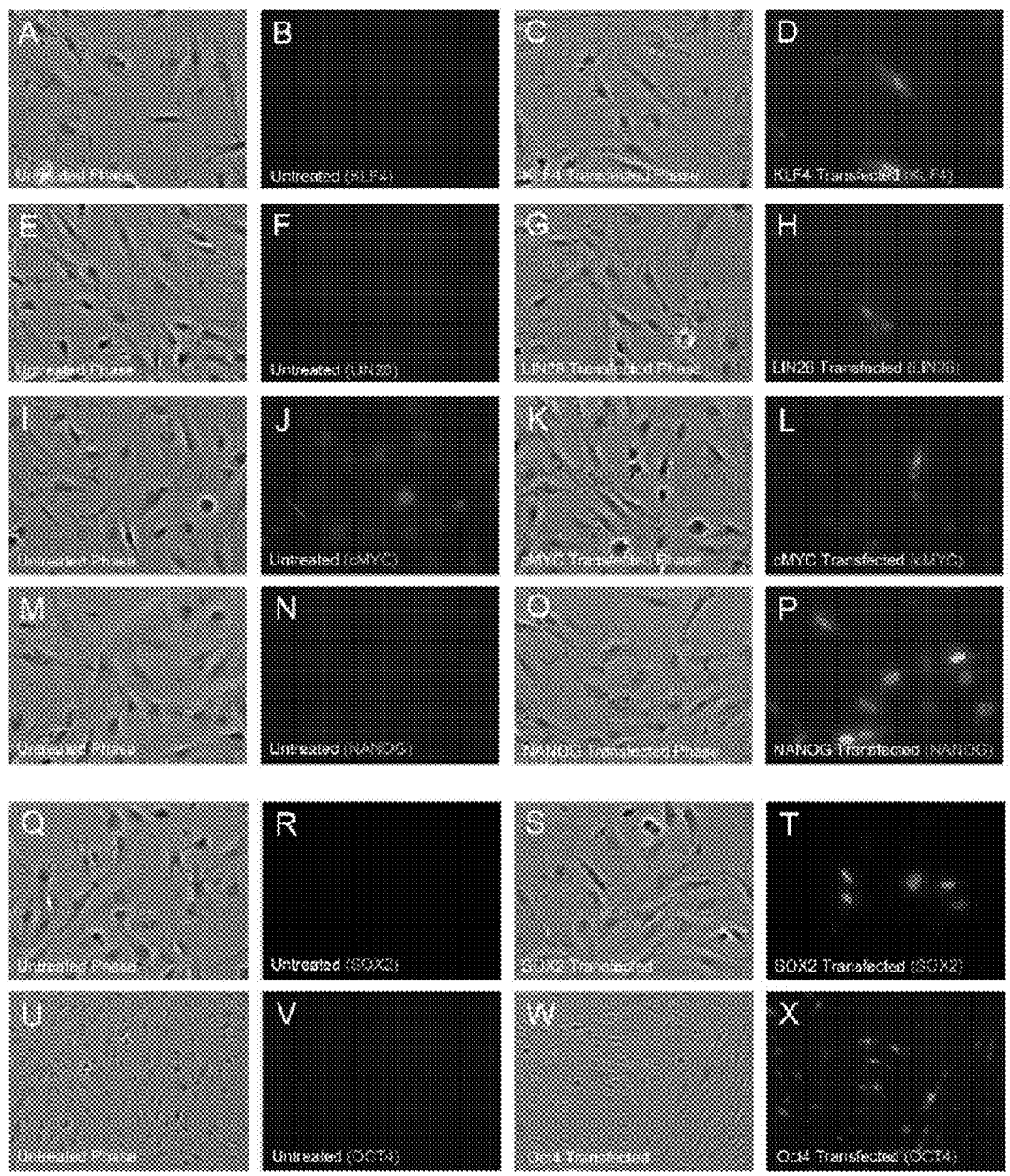
FIG. 1 shows that mRNAs encoding each of the six human reprogramming factors, prepared as described in the EXAMPLES, are expressed when transfected into human newborn 1079 fibroblasts. Phase contrast images of the human 1079 fibroblasts which were not transfected with an mRNA encoding a reprogramming factor (i.e., untreated) and which were not stained with a labeled antibody specific for a reprogramming factor are shown in A, E, I, M, Q, and U. Phase contrast images of untreated human 1079 fibroblasts which were stained using a labeled antibody specific for the indicated reprogramming factor show the endogenous expression of that respective reprogramming factor protein in B, F, J, N, R, and V. Phase contrast images of the human 1079 fibroblasts which were transfected with an mRNA encoding the indicated reprogramming factor (i.e., treated or transfected), but which were not stained with a labeled antibody specific for a reprogramming factor are shown in C, G, K, O, S, and W; and the corresponding images of the human 1079 fibroblasts that were transfected with mRNA encoding the indicated reprogramming factor and then stained with respective labeled antibody specific for that reprogramming factor 24 hours post-transfection are shown in D, H, L, P, T, and X. A-T are at 20× magnification. U-X are at 10× magnification.

The present invention will be understood and interpreted based on terms as defined below.

The terms "comprising", "containing", "having", "include", and "including" are to be construed as "including, but not limited to" unless otherwise noted. The terms "a," "an," and "the" and similar referents in the context of describing the invention and, specifically, in the context of the appended claims, are to be construed to cover both the singular and the plural unless otherwise noted. The use of any and all examples or exemplary language ("for example", "e.g.", "such as") is intended merely to illustrate aspects or embodiments of the invention, and is not to be construed as limiting the scope thereof, unless otherwise claimed.

With respect to the use of the word "derived", such as for an RNA (including mRNA) or a polypeptide that is "derived" from a sample, biological sample, cell, tumor, or the like, it is meant that the RNA or polypeptide either was present in the sample, biological sample, cell, tumor, or the like, or was made using the RNA in the sample, biological sample, cell, tumor, or the like by a process such as an in vitro transcription reaction, or an RNA amplification reaction, wherein the RNA or polypeptide is either encoded by or a copy of all or a portion of the RNA or polypeptide molecules in the original sample, biological sample, cell, tumor, or the like. By way of example, such RNA can be from an in vitro transcription or an RNA amplification reaction, with or without cloning of cDNA, rather than being obtained directly from the sample, biological sample, cell, tumor, or the like, so long as the original RNA used for the in vitro transcription or an RNA amplification reaction was from the sample, biological sample, cell, tumor, or the like.

The terms "sample" and "biological sample" are used in their broadest sense and encompass samples or specimens obtained from any source that contains or may contain eukaryotic cells, including biological and environmental sources. As used herein, the term "sample" when used to refer to biological samples obtained from organisms, includes bodily fluids (e.g., blood or saliva), feces, biopsies, swabs (e.g., buccal swabs), isolated cells, exudates, and the like. The organisms include fungi, plants, animals, and humans. However, these examples are not to be construed as limiting the types of samples or organisms that find use with the present invention. In addition, in order to perform research or study the results related to use of a method or composition of the invention, in some embodiments, a "sample" or "biological sample" comprises fixed cells, treated cells, cell lysates, and the like. In some embodiments, such as embodiments of the method wherein the mRNA is delivered into a cell from an organism that has a known disease or into a cell that exhibits a disease state or a known pathology, the "sample" or "biological sample" also comprises bacteria or viruses.

As used herein, the term "incubating" and variants thereof mean contacting one or more components of a reaction with another component or components, under conditions and for sufficient time such that a desired reaction product is formed.

As used herein, a "nucleoside" refers to a molecule consisting of a guanine (G), adenine (A), thymine (T), uridine (U), pseudouridine (abbreviated by the Greek letter psi-Ψ), or cytidine (C) base covalently linked to a pentose sugar, whereas "nucleotide" or "mononucleotide" refers to a nucleoside phosphorylated at one of the hydroxyl groups of the pentose sugar.

Linear nucleic acid molecules are said to have a "5' terminus" (5' end) and a "3' terminus" (3' end) because, except with respect to adenylation (as described elsewhere herein), mononucleotides are joined in one direction via a phosphodiester linkage to make oligonucleotides, in a manner such that a phosphate on the 5' carbon of one mononucleotide sugar moiety is joined to an oxygen on the 3' carbon of the sugar moiety of its neighboring mononucleotide. Therefore, an end of an oligonucleotide is referred to as the "5' end" if its 5' phosphate is not linked to the oxygen of the 3' carbon of a mononucleotide sugar moiety, and as the "3' end" if its 3' oxygen is not linked to a 5' phosphate of a subsequent mononucleotide sugar moiety. A terminal nucleotide, as used herein, is the nucleotide at the end position of the 3' or 5' terminus.

In order to accomplish specific goals, a nucleic acid base, sugar moiety, or internucleoside linkage in one or more of the nucleotides of the mRNA that is introduced into a eukaryotic cell in any of the methods of the invention may comprise a modified base, sugar moiety, or internucleoside linkage. For example, one or more of the nucleotides of the mRNA can have a modified nucleic acid base comprising or consisting of: xanthine; allyamino-uracil; allyamino-thymidine; hypoxanthine; 2-aminoadenine; 5-propynyl uracil; 5-propynyl cytosine; 4-thiouracil; 6-thioguanine; an aza or deaza uracil; an aza or deaza thymidine; an aza or deaza cytosines; an aza or deaza adenine; or an aza or deaza guanines; or a nucleic acid base that is derivatized with a biotin moiety, a digoxigenin moiety, a fluorescent or chemiluminescent moiety, a quenching moiety or some other moiety. Still further, one or more of the nucleotides of the mRNA can have a sugar moiety, such as, but not limited to: 2'-fluoro-2'-deoxyribose or 2'-O-methyl-ribose, which provide resistance to some nucleases; or 2'-amino-2'-deoxyribose or 2'-azido-2'-deoxyribose, which can be labeled by reacting them with visible, fluorescent, infrared fluorescent or other detectable dyes or chemicals having an electrophilic, photoreactive, alkynyl, or other reactive chemical moiety. Still further, one or more of the nucleotides of the mRNA can have a modified internucleoside linkage, such as, but not limited to, a phosphorothioate, phosphorodithioate, phosphoroselenate, or phosphorodiselenate linkage, which are resistant to some nucleases. The invention is not limited to the modified nucleic acid bases, sugar moieties, or internucleoside linkages listed, but the list is presented to show examples which may be used for a particular purpose in a method.

As used herein, a "nucleic acid" or a "polynucleotide" is a covalently linked sequence of nucleotides in which the 3' position of the sugar moiety of one nucleotide is joined by a phosphodiester bond to the 5' position of the sugar moiety of the next nucleotide (i.e., a 3' to 5' phosphodiester bond), and in which the nucleotides are linked in specific sequence; i.e., a linear order of nucleotides. As used herein, an "oligonucleotide" is a short polynucleotide or a portion of a polynucleotide. For example, but without limitation, an oligonucleotide may be between 10-60 nucleotides in length. In some embodiments, the oligonucleotide consists of or comprises 2'-deoxyribonucleotides (DNA). In some embodiments, the oligonucleotide consists of or comprises ribonucleotides (RNA).

The terms "isolated" or "purified" when used in relation to a polynucleotide or nucleic acid, as in "isolated RNA" or "purified RNA" refers to a nucleic acid that is identified and separated from at least one contaminant with which it is ordinarily associated in its source. Thus, an isolated or purified nucleic acid (e.g., DNA and RNA) is present in a form or setting different from that in which it is found in nature, or a form or setting different from that which existed prior to subjecting it to a treatment or purification method. For example, a given DNA sequence (e.g., a gene) is found on the host cell chromosome together with other genes as well as structural and functional proteins, and a specific RNA (e.g., a specific mRNA encoding a specific protein), is found in the cell as a mixture with numerous other RNAs and other cellular components. The isolated or purified polynucleotide or nucleic acid may be present in single-stranded or double-stranded form.

A "cap" or a "cap nucleotide" means a nucleoside-5'-triphosphate that, under suitable reaction conditions, is used as a substrate by a capping enzyme system and that is thereby joined to the 5'-end of an uncapped RNA comprising primary RNA transcripts or RNA having a 5'-diphosphate. The nucleotide that is so joined to the RNA is also referred to as a "cap nucleotide" herein. A "cap nucleotide" is a guanine nucleotide that is joined through its 5' end to the 5' end of a primary RNA transcript. The RNA that has the cap nucleotide joined to its 5' end is referred to as "capped RNA" or "capped RNA transcript" or "capped transcript." A common cap nucleoside is 7-methylguanosine or $N^7$-methylguanosine (sometimes referred to as "standard cap"), which has a structure designated as "$m^7G$," in which case the capped RNA or "$m^7G$-capped RNA" has a structure designated as $m^7G(5')ppp(5')N_1(pN)_x$—OH(3'), or more simply, as $m^7GpppN_1(pN)_x$ or $m^7G[5']ppp[5']N$, wherein $m^7G$ represents the 7-methylguanosine cap nucleoside, ppp represents the triphosphate bridge between the 5' carbons of the cap nucleoside and the first nucleotide of the primary RNA transcript, $N_1(pN)_x$—OH(3') represents the primary RNA transcript, of which $N_1$ is the most 5'-nucleotide, "p" represents a phosphate group, "G" represents a guanosine nucleoside, "$m^7$" represents the methyl group on the 7-position of guanine, and "[5']" indicates the position at which the "p" is joined to the ribose of the cap nucleotide and the first nucleoside of the mRNA transcript ("N"). In addition to this "standard cap," a variety of other naturally-occurring and synthetic cap analogs are known in the art. RNA that has any cap nucleotide is referred to as "capped RNA." The capped RNA can be naturally occurring from a biological sample or it can be obtained by in vitro capping of RNA that has a 5' triphosphate group or RNA that has a 5' diphosphate group with a capping enzyme system (e.g., vaccinia capping enzyme system or *Saccharomyces cerevisiae* capping enzyme system). Alternatively, the capped RNA can be obtained by in vitro transcription (IVT) of a DNA template that contains an RNA polymerase promoter, wherein, in addition to the GTP, the IVT reaction also contains a dinucleotide cap analog (e.g., a $m^7GpppG$ cap analog or an $N^7$-methyl, 2'-O-methyl-GpppG ARCA cap analog or an $N^7$-methyl, 3'-O-methyl-GpppG ARCA cap analog) using methods known in the art (e.g., using an AMPLICAP™ T7 capping kit (EPICENTRE)).

Capping of a 5'-triphosphorylated primary mRNA transcript in vivo (or using a capping enzyme system in vitro) occurs via several enzymatic steps (Higman et al. 1992, Martin et al. 1975, Myette and Niles 1996).

The following enzymatic reactions are involved in capping of eukaryotic mRNA:

(1) RNA triphosphatase cleaves the 5'-triphosphate of mRNA to a diphosphate,

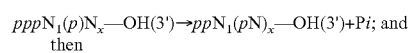
then (2) RNA guanyltransferase catalyzes joining of GTP to the 5'-diphosphate of the most 5' nucleotide ($N_1$) of the mRNA,

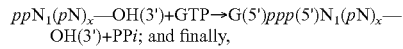
$pp N_1(pN)_x$—OH(3')+GTP→G(5')$ppp$(5')$N_1(pN)_x$— OH(3')+PP$i$; and finally, (3) guanine-7-methyltransferase, using S-adenosyl-methionine (AdoMet) as a co-factor, catalyzes methylation of the 7-nitrogen of guanine in the cap nucleotide,

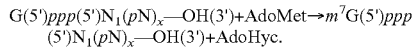
G(5')$ppp$(5')$N_1(pN)_x$—OH(3')+AdoMet→$m^7$G(5')$ppp$ (5')$N_1(pN)_x$—OH(3')+AdoHyc.

RNA that results from the action of the RNA triphosphatase and the RNA guanyltransferase enzymatic activities, as well as RNA that is additionally methylated by the guanine-7-methyltransferase enzymatic activity, is referred to herein as "5' capped RNA" or "capped RNA", and a "capping enzyme system" or, more simply, a "capping enzyme" herein means any combination of one or more polypeptides having the enzymatic activities that result in "capped RNA." Capping enzyme systems, including cloned forms of such enzymes, have been identified and purified from many sources and are well known in the art (Banerjee 1980, Higman et al. 1992, Higman et al. 1994, Myette and Niles 1996, Shuman 1995, Shuman 2001, Shuman et al. 1980, Wang et al. 1997). Any capping enzyme system that can convert uncapped RNA that has a 5' polyphosphate to capped RNA can be used to provide a capped RNA for any of the embodiments of the present invention. In some embodiments, the capping enzyme system is a poxvirus capping enzyme system. In some preferred embodiments, the capping enzyme system is vaccinia virus capping enzyme. In some embodiments, the capping enzyme system is *Saccharomyces cerevisiae* capping enzyme. Also, in view of the fact that genes encoding RNA triphosphatase, RNA guanyltransferase and guanine-7-methyltransferase from one source can complement deletions in one or all of these genes from another source, the capping enzyme system can originate from one source, or one or more of the RNA triphosphatase, RNA guanyltransferase, and/or guanine-7-methyltransferase activities can comprise a polypeptide from a different source.

A "modified cap nucleotide" of the present invention means a cap nucleotide wherein the sugar, the nucleic acid base, or the internucleoside linkage is chemically modified compared to the corresponding canonical 7-methylguanosine cap nucleotide. Examples of a modified cap nucleotide include a cap nucleotide comprising: (i) a modified 2'- or 3'-deoxyguanosine-5'-triphosphate (or guanine 2'- or 3'-deoxyribonucleic acid-5'-triphosphate) wherein the 2'- or 3'-deoxy position of the deoxyribose sugar moiety is substituted with a group comprising an amino group, an azido group, a fluorine group, a methoxy group, a thiol (or mercapto) group or a methylthio (or methylmercapto) group; or (ii) a modified guanosine-5'-triphosphate, wherein the O6 oxygen of the guanine base is substituted with a methyl group; or (iii) 3'-deoxyguanosine. For the sake of clarity, it will be understood herein that an "alkoxy-substituted deoxyguanosine-5'-triphosphate" can also be referred to as an "O-alkyl-substituted guanosine-5'-triphosphate"; by way of example, but without limitation, 2'-methoxy-2'-deoxyguanosine-5'-triphosphate (2'-methoxy-2'-dGTP) and 3'-methoxy-3'-deoxyguanosine-5'-triphosphate (3'-methoxy-3'-dGTP) can also be referred to herein as 2'-O-methylguanosine-5'-triphosphate (2'-OMe-GTP) and 3'-O-methylguanosine-5'-triphosphate (3'-OMe-GTP), respectively. Following joining of the modified cap nucleotide to the 5'-end of the uncapped RNA comprising primary RNA transcripts (or RNA having a 5'-diphosphate), the portion of said modified cap nucleotide that is joined to the uncapped RNA comprising primary RNA transcripts (or RNA having a 5'-diphosphate) may be referred to herein as a "modified cap nucleoside" (i.e., without referring to the phosphate groups to which it is joined), but sometimes it is referred to as a "modified cap nucleotide".

A "modified-nucleotide-capped RNA" is a capped RNA molecule that is synthesized using a capping enzyme system and a modified cap nucleotide, wherein the cap nucleotide on its 5' terminus comprises the modified cap nucleotide, or a capped RNA that is synthesize co-transcriptionally in an in vitro transcription reaction that contains a modified dinucleotide cap analog wherein the dinucleotide cap analog contains the chemical modification in the cap nucleotide. In some embodiments, the modified dinucleotide cap analog is an anti-reverse cap analog or ARCA (Grudzien et al. 2004, Grudzien-Nogalska et al. 2007, Jemielity et al. 2003, Peng et al. 2002, Stepinski et al. 2001).

A "primary RNA" or "primary RNA transcript" means an RNA molecule that is synthesized by an RNA polymerase in vivo or in vitro and which RNA molecule has a triphosphate on the 5'-carbon of its most 5' nucleotide.

An "RNA amplification reaction" or an "RNA amplification method" means a method for increasing the amount of RNA corresponding to one or multiple desired RNA sequences in a sample. For example, in some embodiments, the RNA amplification method comprises: (a) synthesizing first-strand cDNA complementary to the one or more desired RNA molecules by RNA-dependent DNA polymerase extension of one or more primers that anneal to the desired RNA molecules; (b) synthesizing double-stranded cDNA from the first-strand cDNA using a process wherein a functional RNA polymerase promoter is joined thereto; and (c) contacting the double-stranded cDNA with an RNA polymerase that binds to said promoter under transcription conditions whereby RNA corresponding to the one or more desired RNA molecules is obtained. Unless otherwise stated related to a specific embodiment of the invention, an RNA amplification reaction according to the present invention means a sense RNA amplification reaction, meaning an RNA amplification reaction that synthesizes sense RNA (e.g., RNA having the same sequence as an mRNA or other primary RNA transcript, rather than the complement of that sequence). Sense RNA amplification reactions known in the art, which are encompassed within this definition include, but are not limited to, the methods which synthesize sense RNA described in Ozawa et al. (Ozawa et al. 2006) and in U.S. Patent Application Nos. 20090053775; 20050153333; 20030186237; 20040197802; and 20040171041. The RNA amplification method described in U.S. Patent Application No. 20090053775 is a preferred method for obtaining amplified RNA derived from one or more cells, which amplified RNA is then used to make mRNA for use in the methods of the present invention.

A "poly-A polymerase" ("PAP") means a template-independent RNA polymerase found in most eukaryotes, prokaryotes, and eukaryotic viruses that selectively uses ATP to incorporate AMP residues to 3'-hydroxylated ends of RNA. Since PAP enzymes that have been studied from plants, animals, bacteria and viruses all catalyze the same overall reaction (Edmonds 1990) are highly conserved structurally (Gershon 2000) and lack intrinsic specificity for particular sequences or sizes of RNA molecules if the PAP is separated from proteins that recognize AAUAAA polyadenylation signals (Wilusz and Shenk 1988), purified wild-type and recombinant PAP enzymes from any of a variety of sources can be used for the present invention.

A "reprogramming factor" means a protein, peptide, or other biomolecule that, when used alone or in combination with other factors or conditions, causes a change in the state of differentiation of a cell in which the reprogramming factor is introduced or expressed. In some preferred embodiments of the methods of the present invention, the reprogramming factor is a protein or peptide that is encoded by an mRNA that is introduced into a cell, thereby generating a cell that exhibits a changed state of differentiation compared to the cell in which the mRNA was introduced. In some preferred embodiments of the methods of the present invention, the reprogramming factor is a transcription factor. One embodiment of a reprogramming factor used in a method of the present invention is an "iPS induction factor."

An "iPS cell induction factor" is a protein, peptide, or other biomolecule that, when used alone or in combination with other dedifferentiation factors, causes the generation of iPS cells from somatic cells. Examples of iPS cell induction factors include OCT4, SOX2, c-MYC, KLF4, NANOG and LIN28. iPS cell induction factors include full length polypeptide sequences or biologically active fragments thereof. Likewise an mRNA encoding an iPS cell induction factor may encode a full length polypeptide or biologically active fragments thereof. The mRNA coding sequence for exemplary iPS induction factors are shown in FIG. 6 (KLF4 and LIN28), 7 (cMYC and NANOG), and 8 (OCT4 and SOX2). In certain embodiments, the present invention employs the sequences or similar sequences shown in these figures, including mRNA molecules that additionally comprise, joined to these mRNA sequences, oligoribonucleotides which exhibit any of the 5' and 3' UTR sequences, Kozak sequences, IRES sequences, cap nucleotides, and/or poly(A) sequences used in the experiments described herein, or which are generally known in the art and which can be used in place of those used herein by joining them to these protein-coding mRNA sequences for the purpose of optimizing translation of the respective mRNA molecules in the cells and improving their stability in the cell in order to accomplish the methods described herein.

"Differentiation" or "cellular differentiation" means the process by which a cell that exhibits a less specialized state of differentiation or cell type becomes a cell that exhibits a more specialized state of differentiation or cell type. Scientists, including biologists, cell biologists, immunologists, and embryologists, use a variety of methods and criteria to define, describe, or categorize different cells according to their "cell type," "differentiated state," or "state of differentiation." In general, a cell is defined, described, or categorized with respect to its "cell type," "differentiated state," or "state of differentiation" based on one or more phenotypes exhibited by that cell, which phenotypes can include shape, a biochemical or metabolic activity or function, the presence of certain biomolecules in the cell (e.g., based on stains that react with specific biomolecules), or on the cell (e.g., based on binding of one or more antibodies that react with specific biomolecules on the cell surface). For example, in some embodiments, different cell types are identified and sorted using a cell sorter or fluorescent-activated cell sorter (FACS) instrument.

"Dedifferentiation" means the process by which a cell that exhibits a more specialized state of differentiation or cell type becomes a cell that exhibits a less specialized state of differentiation or cell type. For example, in some preferred embodiments of the method of the present invention, a differentiated somatic cell (e.g., a mammalian fibroblast) is dedifferentiated into an iPS cell, meaning that the somatic cell loses the more specialized state of differentiation and becomes an iPS cell that exhibits a less specialized state of differentiation.

DESCRIPTION OF THE INVENTION

The present invention relates to compositions and methods for reprogramming somatic cells to pluripotent stem cells. For example, the present invention provides mRNA molecules and their use to reprogram human somatic cells into pluripotent stem cells.

Experiments conducted during the development of embodiments of the present invention demonstrated that mRNA molecules can be administered to cells and induce a dedifferentiation process to generate dedifferentiated cells—including pluripotent stem cells. Thus, the present invention provides compositions and methods for generating iPS cells. Surprisingly, the administration of mRNA can provide highly efficient generation of iPS cells.

In some embodiments, the present invention provides methods for dedifferentiating a somatic cell comprising: introducing mRNA encoding one or more iPSC induction factors into a somatic cell to generate a dedifferentiated cell.

In some embodiments, the present invention provides methods for dedifferentiating a somatic cell comprising: introducing mRNA encoding one or more iPSC induction factors into a somatic cell and maintaining the cell under conditions wherein the cell is viable and the mRNA that is introduced into the cell is expressed in sufficient amount and for sufficient time to generate a dedifferentiated cell. In some preferred embodiments, the dedifferentiated cell is an induced pluripotent stem cell (iPSC).

In some embodiments, the present invention provides methods for changing the state of differentiation (or differentiated state) of a eukaryotic cell comprising: introducing mRNA encoding one or more reprogramming factors into a cell and maintaining the cell under conditions wherein the cell is viable and the mRNA that is introduced into the cell is expressed in sufficient amount and for sufficient time to generate a cell that exhibits a changed state of differentiation compared to the cell into which the mRNA was introduced.

In some embodiments, the present invention provides methods for changing the state of differentiation of a eukaryotic cell comprising: introducing mRNA encoding one or more reprogramming factors into a cell and maintaining the cell under conditions wherein the cell is viable and the mRNA that is introduced into the cell is expressed in sufficient amount and for sufficient time to generate a cell that exhibits a changed state of differentiation compared to the cell into which the mRNA was introduced. In some embodiments, the changed state of differentiation is a dedifferentiated state of differentiation compared to the cell into which the mRNA was introduced. For example, in some embodiments, the cell that exhibits the changed state of differentiation is a pluripotent stem cell that is dedifferentiated compared to a somatic cell into which the mRNA was introduced (e.g., a somatic cell that is differentiated into a fibroblast, a cardomyocyte, or another differentiated cell type). In some embodiments, the cell into which the mRNA is introduced is a somatic cell of one lineage, phenotype, or function, and the cell that exhibits the changed state of differentiation is a somatic cell that exhibits a lineage, phenotype, or function that is different than that of the cell into which the mRNA was introduced; thus, in these embodiments, the method results in transdifferentiation (Graf and Enver 2009).

The methods of the invention are not limited with respect to a particular cell into which the mRNA is introduced. In some embodiments of any of the above methods, the cell into which the mRNA is introduced is derived from any multi-cellular eukaryote. In some embodiments of any of the above methods, the cell into which the mRNA is introduced is selected from among a human cell, an animal cell, a plant cell, and a fungal cell. In some embodiments of any of the above methods, the cell into which the mRNA is introduced is a normal cell that is from an organism that is free of a known disease. In some embodiments of any of the above methods, the cell into which the mRNA is introduced is a cell from an organism that has a known disease. In some embodiments of any of the above methods, the cell into which the mRNA is introduced is a cell that is free of a known pathology. In some embodiments of any of the above methods, the cell into which the mRNA is introduced is a cell that exhibits a disease state or a known pathology (e.g., a cancer cell, or a pancreatic beta cell that exhibits metabolic properties characteristic of a diabetic cell).

The invention is not limited to the use of a specific cell type (e.g., to a specific somatic cell type) in embodiments of the methods comprising introducing mRNA encoding one or more iPSC cell induction factors in order to generate a dedifferentiated cell (e.g., an iPS cell). Any cell that is subject to dedifferentiation using iPS cell induction factors is contemplated. Such cells include, but are not limited to, fibroblasts, keratinocytes, adipocytes, lymphocytes, T-cells, B-Cells, cells in mononuclear cord blood, buccal mucosa cells, hepatic cells, HeLa, MCF-7 or other cancer cells. In some embodiments, the cells reside in vitro (e.g., in culture) or in vivo. In some embodiments, when generated in culture, a cell-free conditioned medium (e.g., MEF-conditioned medium) is used. As demonstrated below, such a medium provided enhanced iPS cell generation. The invention is not limited, however, to the culturing conditions used. Any culturing condition or medium now known or later identified as useful for the methods of the invention (e.g., to generate iPS cells from somatic cells and maintain said cells) is contemplated for use with the invention. For example, although not preferred, in some embodiments of the method, a feeder cell layer is used instead of conditioned medium for culturing the cells that are treated using the method.

In some embodiments of any of these methods, the step of introducing mRNA comprises delivering the mRNA into the cell (e.g., a human or other animal somatic cell) with a transfection reagent (e.g., TRANSIT™ mRNA transfection reagent, MirusBio, Madison, Wis.). However, the invention is not limited by the nature of the transfection method utilized. Indeed, any transfection process known, or identified in the future that is able to deliver mRNA molecules into cells in vitro or in vivo, is contemplated, including methods that deliver the mRNA into cells in culture or in a life-supporting medium, whether said cells comprise isolated cells or cells comprising a eukaryotic tissue or organ, or methods that deliver the mRNA in vivo into cells in an organism, such as a human, animal, plant or fungus. In some embodiments, the transfection reagent comprises a lipid (e.g., liposomes, micelles, etc.). In some embodiments, the transfection reagent comprises a nanoparticle or nanotube. In some embodiments, the transfection reagent comprises a cationic compound (e.g., polyethylene imine or PEI). In some embodiments, the transfection method uses an electric current to deliver the mRNA into the cell (e.g., by electroporation).

The data presented herein shows that, with respect to the mRNA introduced into the cell, certain amounts of the mRNAs used in the EXAMPLES described herein resulted in higher efficiency and more rapid induction of pluripotent stem cells from the particular somatic cells used than other amounts of mRNA. However, the methods of the present invention are not limited to the use of a specific amount of mRNA to introduce into the cell. For example, in some embodiments, a total of three doses, with each dose comprising 18 micrograms of each of six different mRNAs, each encoding a different human reprogramming factor, was used to introduce the mRNA into approximately $3 \times 10^5$ human fibroblast cells in a 10-cm plate (e.g., delivered using a lipid-containing transfection reagent), although in other embodiments, higher or lower amounts of the mRNAs were used to introduce into the cells.

The invention is not limited to a particular chemical form of the mRNA used, although certain forms of mRNA may produce more efficient results. In some embodiments, the mRNA is polyadenylated. For example, in some preferred embodiments, the mRNA comprises a poly-A tail (e.g., a poly-A tail having 50-200 nucleotides, e.g., preferably 100-200, 150-200 nucleotides, or greater than 150 nucleotides), although in some embodiments, a longer or a shorter poly-A tail is used. In some embodiments, the mRNA used in the methods is capped. To maximize efficiency of expression in the cells, it is preferred that the majority of mRNA molecules contain a cap. In some preferred embodiments, the mRNA molecules used in the methods are synthesized in vitro by incubating uncapped primary RNA in the presence of with a capping enzyme system. In some preferred embodiments, the primary RNA used in the capping enzyme reaction is synthesized by in vitro transcription (IVT) of a DNA molecule that encodes the RNA to be synthesized. The DNA that encodes the RNA to be synthesized is joined to an RNA polymerase promoter, to which, an RNA polymerase binds and initiates transcription therefrom. The IVT can be performed using any RNA polymerase so long as synthesis of the template that encodes the RNA is specifically and sufficiently initiated from a respective cognate RNA polymerase promoter. In some preferred embodiments, the RNA polymerase is selected from among T7 RNA polymerase, SP6 RNA polymerase and T3 RNA polymerase. In some other embodiments, capped RNA is synthesized co-transcriptionally by using a dinucleotide cap analog in the IVT reaction (e.g., using an AMPLICAP™ T7 Kit; EPICENTRE Technologies Corporation, Madison, Wis.). However, use of a separate IVT reaction, followed by capping with a capping enzyme system, which results in approximately 100% of the RNA being capped, is preferred over co-transcriptional capping, which typically results in only about 80% of the RNA being capped. Thus, in some preferred embodiments, a high percentage of the mRNA molecules used in a method of the present invention are capped (e.g., greater than 80%, greater than 90%, greater than 95%, greater than 98%, greater than 99%, greater than 99.5%, or greater than 99.9% of the population of mRNA molecules are capped). In some preferred embodiments, the mRNA used in the methods of the present invention has a cap with a cap1 structure, meaning that the penultimate nucleotide with respect to the cap nucleotide has a methyl group on the 2'-position of the ribose. However, in some embodiments, mRNA used in the methods has a cap with a cap0 structure, meaning that the penultimate nucleotide with respect to the cap nucleotide does not have a methyl group on the 2'-position of the ribose. With some but not all transcripts, transfection of eukaryotic cells with mRNA having a cap with a cap1 structure results in a higher level or longer duration of protein expression in the transfected cells compared to transfection of the same cells with the same mRNA but with a cap having a cap0 structure. In some embodiments, the mRNA used in the methods of the present invention has a modified cap nucleotide. In some experiments performed prior to the experiments presented in the EXAMPLES herein, the present Applicants found that, when 1079 or IMR90 human fibroblast cells were transfected with OCT4 mRNA that contained either uridine or pseudouridine in place of uridine, the pseudouridine-containing mRNA was expressed at a higher level or for a longer duration than the mRNA that contained uridine. Therefore, in some preferred embodiments, one or more or all of the uridines contained in the mRNA(s) used in the methods of the present invention is/are replaced by pseudouridine (e.g., by substituting pseudouridine-5'-triphosphate in the IVT reaction to synthesize the RNA in place of uridine-5'-triphosphate). However, in some embodiments, the mRNA used in the methods of the invention contains uridine and does not contain pseudouridine. In addition, in order to accomplish specific goals, a nucleic acid base, sugar moiety, or internucleoside linkage in one or more of the nucleotides of the mRNA that is introduced into a eukaryotic cell in any of the methods of the invention may comprise a modified nucleic acid base, sugar moiety, or internucleoside linkage.

The invention is also not limited with respect to the source of the mRNA that is delivered into the eukaryotic cell in any of the methods of the invention. In some embodiments, such as those described in the EXAMPLES, the mRNA is synthesized in vitro by transcription of a DNA template comprising a gene cloned in a linearized plasmid vector or a PCR or RT-PCR amplification product, capping using a capping enzyme system, and polyadenylation using a poly-A polymerase. In some other embodiments, the mRNA that is delivered into the eukaryotic cell in any of the methods of the invention is derived directly from a cell or a biological sample. For example, in some embodiments, the mRNA derived from a cell or biological sample is obtained by amplifying the mRNA from the cell or biological sample using an RNA amplification reaction.

With respect to the methods comprising introducing mRNA encoding one or more iPSC cell induction factors in order to generate a dedifferentiated cell (e.g., an iPS cell), the invention is not limited by the nature of the iPS cell induction factors used. Any mRNA encoding one or more protein induction factors now known, or later discovered, that find use in dedifferentiation, are contemplated for use in the present invention. In some embodiments, one or more mRNAs encoding for KLF4, LIN28, c-MYC, NANOG, OCT4, or SOX2 are employed. Oct-3/4 and certain members of the Sox gene family (Sox1, Sox2, Sox3, and Sox15) have been identified as transcriptional regulators involved in the induction process. Additional genes, however, including certain members of the Klf family (Klf1, Klf2, Klf4, and Klf5), the Myc family (C-myc, L-myc, and N-myc), Nanog, and LIN28, have been identified to increase the induction efficiency. Any one or more such factors may be used as desired.

While the compositions and methods of the invention may be used to generated iPS cells, the invention is not limited to the generation of such cells. For example, in some embodiments, mRNA encoding one or more reprogramming factors is introduced into a cell in order to generate a cell with a changed state of differentiation compared to the cell into which the mRNA was introduced. For example, in some embodiments, mRNA encoding one or more iPS cell induction factors is used to generate a dedifferentiated cell that is not an iPS cells. Such cells find use in research, drug screening, and other applications.

In some embodiments, the present invention further provides methods employing the dedifferentiated cells generated by the above methods. For example, such cells find use in research, drug screening, and therapeutic applications in humans or other animals. For example, in some embodiments, the cells generated find use in the identification and characterization of iPS cell induction factors as well as other factors associated with differentiation or dedifferentiation. In some embodiments, the generated dedifferentiated cells are transplanted into an organism or into a tissue residing in vitro or in vivo. In some embodiments, an organism, tissue, or culture system housing the generated cells is exposed to a test compound and the effect of the test compound on the cells or on the organism, tissue, or culture system is observed or measured.

In some other embodiments, a dedifferentiated cell generated using the above methods (e.g., an iPS cell) is further treated to generate a differentiated cell that has the same state of differentiation or cell type compared to the somatic cell from which the dedifferentiated cell was generated. In some other embodiments, the dedifferentiated cell generated using the above methods (e.g., an iPS cell) is further treated to generate a differentiated cell that has a different state of differentiation or cell type compared to the somatic cell from which the dedifferentiated cell was generated. In some embodiments, the differentiated cell is generated from the generated dedifferentiated cell (e.g., the generated iPS cell) by introducing mRNA encoding one or more reprogramming factors into the generated iPS cell and maintaining the cell into which the mRNA is introduced under conditions wherein the cell is viable and is differentiated into a cell that has a changed state of differentiation or cell type compared to the generated dedifferentiated cell (e.g., the generated iPS cell) into which the mRNA encoding the one or more reprogramming factors is introduced. In some of these embodiments, the generated differentiated cell that has the changed state of differentiation is used for research, drug screening, or therapeutic applications (e.g., in humans or other animals). For example, the generated differentiated cells find use in the identification and characterization of reprogramming factors associated with differentiation. In some embodiments, the generated differentiated cells are transplanted into an organism or into a tissue residing in vitro or in vivo. In some embodiments, an organism, tissue, or culture system housing the generated differentiated cells is exposed to a test compound and the effect of the test compound on the cells or on the organism, tissue, or culture system is observed or measured.

In some preferred embodiments of the method comprising introducing mRNA encoding one or more iPSC induction factors into a somatic cell and maintaining the cell under conditions wherein the cell is viable and the mRNA that is introduced into the cell is expressed in sufficient amount and for sufficient time to generate a dedifferentiated cell (e.g., wherein the dedifferentiated cell is an induced pluripotent stem cell), the sufficient time to generate a dedifferentiated cell is less than one week. In some preferred embodiments of this method, the reprogramming efficiency for generating dedifferentiated cells is greater than or equal to 50 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 100 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 150 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 200 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 300 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 400 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 500 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 600 dedifferentiated cells per $3 \times 10^5$ input cells (e.g., iPSCs) into which the mRNA is introduced. In some preferred embodiments of this method, the reprogramming efficiency for generating dedifferentiated cells is greater than or equal to 700 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 800 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 900 dedifferentiated cells (e.g., iPSCs) per $3 \times 10^5$ input cells into which the mRNA is introduced. In some preferred embodiments of this method, the reprogramming efficiency for generating dedifferentiated cells is greater than or equal to 1000 dedifferentiated cells (e.g., iPSCs) per $3 \times 10^5$ input cells into which the mRNA is introduced. Thus, in some preferred embodiments, this method was greater than 2-fold more efficient than the published protocol comprising delivery of reprogramming factors with a viral vector (e.g., a lentivirus vector). In some preferred embodiments, this method was greater than 5-fold more efficient than the published protocol comprising delivery of reprogramming factors with a viral vector (e.g., a lentivirus vector). In some preferred embodiments, this method was greater than 10-fold more efficient than the published protocol comprising delivery of reprogramming factors with a viral vector (e.g., a lentivirus vector). In some preferred embodiments, this method was greater than 20-fold more efficient than the published protocol comprising delivery of reprogramming factors with a viral vector (e.g., a lentivirus vector). In some preferred embodiments, this method was greater than 25-fold more efficient than the published protocol comprising delivery of reprogramming factors with a viral vector (e.g., a lentivirus vector). In some preferred embodiments, this method was greater than 30-fold more efficient than the published protocol comprising delivery of reprogramming factors with a viral vector (e.g., a lentivirus vector). In some preferred embodiments, this method was greater than 35-fold more efficient than the published protocol comprising delivery of reprogramming factors with a viral vector (e.g., a lentivirus vector). In some preferred embodiments, this method was greater than 40-fold more efficient than the published protocol comprising delivery of reprogramming factors with a viral vector (e.g., a lentivirus vector).

The present invention further provides compositions (systems, kits, reaction mixtures, cells, mRNA) used or useful in the methods and/or generated by the methods described herein. For example, in some embodiments, the present invention provides an mRNA encoding an iPS cell induction factor, the mRNA having pseudouridine in place of uridine.

The present invention further provides compositions comprising a transfection reagent and an mRNA encoding an iPS cell induction factor (e.g., a mixture of transfection reagent and mRNA).

In some embodiments, the compositions comprise mRNA encoding a plurality (e.g., 2 or more, 3 or more, 4 or more, 5 or more, or 6) of iPS cell induction factors, including, but not limited to, KLF4, LIN28, c-MYC, NANOG, OCT4, and SOX2.

The compositions may further comprise any other reagent or component sufficient, necessary, or useful for practicing any of the methods described herein. Such reagents or components include, but are not limited to, transfection reagents, culture medium (e.g., MEF-condition medium), cells (e.g., somatic cells, iPS cells), containers, boxes, buffers, inhibitors (e.g., RNase inhibitors), labels (e.g., fluorescent, luminescent, radioactive, etc.), positive and/or negative control molecules, reagents for generating capped mRNA, dry ice or other refrigerants, instructions for use, cell culture equipment, detection/analysis equipment, and the like.

In certain embodiments, the mRNAs are purified into purified RNA preparations that have most of the contaminating RNA molecules removed (e.g., molecules that cause an immunogenic response in the cells), such as described in U.S. application Ser. No. 12/962,468 filed Dec. 7, 2010, which is herein incorporated by reference. In certain embodiments, the mRNA used in the purified RNA preparations is purified to remove substantially, essentially, or virtually all of the contaminants, including substantially, essentially, or virtually all of the RNA contaminants. The present invention is not limited with respect to the purification methods used to purify the mRNA, and the invention includes use of any method that is known in the art or developed in the future in order to purify the mRNA and remove contaminants, including RNA contaminants, that interfere with the intended use of the mRNA. For example, in preferred embodiments, the purification of the mRNA removes contaminants that are toxic to the cells (e.g., by inducing an innate immune response in the cells, or, in the case of RNA contaminants comprising double-stranded RNA, by inducing RNA interference (RNAi), e.g., via siRNA or long RNAi molecules) and contaminants that directly or indirectly decrease translation of the mRNA in the cells). In some embodiments, the mRNA is purified by HPLC using a method described herein, including in the Examples. In certain embodiments, the mRNA is purified using on a polymeric resin substrate comprising a C18 derivatized styrene-divinylbenzene copolymer and a triethylamine acetate (TEAA) ion pairing agent is used in the column buffer along with the use of an acetonitrile gradient to elute the mRNA and separate it from the RNA contaminants in a size-dependent manner; in some embodiments, the mRNA purification is performed using HPLC, but in some other embodiments a gravity flow column is used for the purification. In some embodiments, the mRNA is purified using a method described in the book entitled "RNA Purification and Analysis" by Douglas T. Gjerde, Lee Hoang, and David Hornby, published by Wiley-VCH, 2009, herein incorporated by reference. In some embodiments, the mRNA purification is carried out in a non-denaturing mode (e.g., at a temperature less than about 50 degrees C., e.g., at ambient temperature). In some embodiments, the mRNA purification is carried out in a partially denaturing mode (e.g., at a temperature less than about 50 degrees C. and 72 degrees C.). In some embodiments, the mRNA purification is carried out in a denaturing mode (e.g., at a temperature greater than about 72 degrees C.). Of course, those with knowledge in the art will know that the denaturing temperature depends on the melting temperature (Tm) of the mRNA that is being purified as well as on the melting temperatures of RNA, DNA, or RNA/DNA hybrids which contaminate the mRNA. In some other embodiments, the mRNA is purified as described by Mellits K H et al. (Removal of double-stranded contaminants from RNA transcripts: synthesis of adenovirus VA RNA1 from a T7 vector. Nucleic Acids Research 18: 5401-5406, 1990, herein incorporated by reference in its entirety). These authors used a three step purification to remove the contaminants which may be used in embodiments of the present invention. Step 1 was 8% polyacrylamide gel electrophoresis in 7M urea (denaturing conditions). The major RNA band was excised from the gel slice and subjected to 8% polyacrylamide gel electrophoresis under nondenaturing condition no urea) and the major band recovered from the gel slice. Further purification was done on a cellulose CF-11 column using an ethanol-salt buffer mobile phase which separates double stranded RNA from single stranded RNA (Franklin R M. 1966. Proc. Natl. Acad. Sci. USA 55: 1504-1511; Barber R. 1966. Biochem. Biophys. Acta 114:422; and Zelcer A et al. 1982. J. Gen. Virol. 59: 139-148, all of which are herein incorporated by reference) and the final purification step was cellulose chromatography. In some other embodiments, the mRNA is purified using an hydroxylapatite (HAP) column under either non-denaturing conditions or at higher temperatures (e.g., as described by Pays E. 1977. Biochem. J. 165: 237-245; Lewandowski L J et al. 1971. J. Virol. 8: 809-812; Clawson G A and Smuckler E A. 1982. Cancer Research 42: 3228-3231; and/or Andrews-Pfannkoch C et al. 2010. Applied and Environmental Microbiology 76: 5039-5045, all of which are herein incorporated by reference). In some other embodiments, the mRNA is purified by weak anion exchange liquid chromatography under non-denaturing conditions (e.g., as described by Easton L E et al. 2010. RNA 16: 647-653 to clean up in vitro transcription reactions, herein incorporated by reference). In some embodiments, the mRNA is purified using a combination of any of the above methods or another method known in the art or developed in the future. In still another embodiment, the mRNA used in the compositions and methods of the present invention is purified using a process which comprises treating the mRNA with an enzyme that specifically acts (e.g., digests) one or more contaminant RNA or contaminant nucleic acids (e.g., including DNA), but which does not act on (e.g., does not digest) the desired mRNA. For example, in some embodiments, the mRNA used in the compositions and methods of the present invention is purified using a process which comprises treating the mRNA with a ribonuclease III (RNase III) enzyme (e.g., E. coli RNase III) and the mRNA is then purified away from the RNase III digestion products. A ribonuclease III (RNase III) enzyme herein means an enzyme that digests double-stranded RNA greater than about twelve basepairs to short double-stranded RNA fragments. In some embodiments, the mRNA used in the compositions and methods of the present invention is purified using a process which comprises treating the mRNA with one or more other enzymes that specifically digest one or more contaminant RNAs or contaminant nucleic acids (e.g., including DNA).

EXAMPLES

The following experimental protocols were employed in the examples provided below, unless indicated otherwise.

Cell Culture.

Newborn human foreskin fibroblast 1079 cells (Cat# CRL-2097, ATCC, Manassas, Va.) and human IMR90 cells (Cat# CCL-186, ATCC) were cultured in Advanced MEM Medium (Invitrogen, Carlsbad, Calif.) supplemented with 10% heat-inactivated fetal bovine serum (FBS, Hyclone Laboratories, Logan, Utah), 2 mM Glutamax (Invitrogen), 0.1 mM β-mercaptoethanol (Sigma, St. Louis, Mo.), and Penicillin/Streptomycin (Invitrogen). All cells were grown at 37° C. and 5% $CO_2$. In some experiments, human iPS cells that were induced using methods described herein were maintained on irradiated mouse embryonic fibroblasts (MEFs) (R&D Systems, Minneapolis, Minn.) on 10-cm plates pre-coated with 0.1% gelatin (Millipore, Phillipsburg, N.J.) in DMEM/F12 medium supplemented with 20% KnockOut serum replacer, 0.1 mM L-glutamine (all from Invitrogen), 0.1 mM β-mercaptoethanol (Sigma) and 100 ng/ml basic fibroblast growth factor (Invitrogen). In some experiments, human iPS cells that were induced using methods described herein were maintained in MEF-conditioned medium that had been collected as previously described (Xu et al. 2001).

Constructions of Vectors.

The cDNAs for the open reading frames (ORFs) of KLF4, LIN28, NANOG, and OCT4 were PCR amplified from cDNA clones (Open Biosystems, Huntsville, Ala.), cloned into a plasmid vector downstream of a T7 RNA polymerase promoter (Mackie 1988, Studier and Moffatt 1986) (e.g., various pBluescript™, Agilent, La Jolla, Calif. or pGEM™, Promega, Madison, Wis., vectors) and sequenced. The ORF of SOX2 was PCR amplified from a cDNA clone (Invitrogen) and the ORF of c-MYC was isolated by RT-PCR from HeLa cell total RNA. Both SOX2 and c-MYC ORF were also cloned into a plasmid vector downstream of a T7 RNA polymerase promoter and sequenced.

Alternative plasmid vectors containing human open reading frames of (KLF4, LIN28, c-MYC, NANOG, OCT4 and SOX2) were cloned into pBluescriptII. These pBluescriptII vectors where constructed by ligating the above open reading frames into the EcoRV (cMyc) or EcoRV/SpeI (KLF4, LIN28, NANOG, OCT4, and SOX2) sites between the 5' and 3' *Xenopus laevis* B-globin untranslated regions described (Krieg and Melton 1984).

mRNA Production.

The T7 RNA polymerase promoter-containing plasmid contructs (pT7-KLF4, pT7-LIN28, pT7-c-MYC, pT7-OCT4, pT7-SOX2, or pT7-XBg-KLF4, pT7-XBg-LIN28, pT7-XBg-c-MYC, pT7-XBg-OCT4, and pT7-XBg-SOX2) were linearized with BamHI and pT7-NANOG and pT7-XBg-NANOG were linearized with Xba I. The mSCRIPT™ mRNA production system (EPICENTRE Technologies Corporation, Madison, Wis.) was used to produce mRNA with a 5' Cap1 structure and a 3' Poly (A) tail (e.g., with approximately 150 A residues), except that pseudouridine-5'-triphosphate (TRILINK, San Diego, Calif.) was used in place of uridine-5'-triphosphate in the T7 RNA polymerase in vitro transcription reactions.

Reprogramming of Human Somatic Cells on MEFs.

1079 fibroblasts were plated at $1 \times 10^5$ cells/well of a 6-well dish pre-coated with 0.1% gelatin (Millipore) and grown overnight. The 1079 fibroblasts were transfected with equal amounts of each reprogramming factor mRNA (KLF4, LIN28, c-MYC, NANOG, OCT4, and SOX2) using TransIT mRNA transfection reagent (MirusBio, Madison, Wis.). A total of three transfections were performed, with one transfection being performed every other day, with media changes the day after the first and second transfection. The day after the third transfection, the cells were trypsinized and $3.3 \times 10^5$ cells were plated in 1079 medium onto 0.1% gelatin pre-coated 10-cm plate seeded with $7.5 \times 10^5$ MEFs the day before. The day after plating the transfected 1079 fibroblasts onto MEFs, the medium was changed to iPS cell medium.

The iPS cell medium was changed every day. Eight days after plating the transfected cells onto MEFs, MEF-conditioned medium was used. MEF conditioned medium was collected as previously described (Xu et al. 2001). Plates were screened every day for the presence of colonies with an iPS morphology using an inverted microscope.

Alternative protocols for reprogramming 1079 and IMR90 fibroblasts on MEFs were also used. MEFs were plated at $1.25 \times 10^5$ cells/well of a 0.1% gelatin pre-coated 6 well dish and incubated overnight in complete fibroblast media. 1079 or IMR90 fibroblasts were plated at 3×104 cells/well of a 6 well dish seeded with MEFs the previous day and grown overnight at 37° C./5% $CO_2$. The mScript Kit was then used to generate Cap1/poly-adenylated mRNA from the following vectors (pT7-Xβg-KLF4, pT7-Xβg-LIN28, pT7-Xβg-c-MYC, pT7-Xβg-NANOG, pT7-Xβg-OCT4, and pT7-Xβg-SOX2) for use in these daily transfections. All six reprogramming mRNAs were diluted to 100 ng/μl of each mRNA. Equal molarity of each mRNA was added together using the following conversion factors (OCT4 is set at 1 and all of the other mRNAs are multiplied by these conversion factors to obtain equal molarity in each mRNA mix). KLF=1.32, LIN28=0.58, c-MYC=1.26, NANOG=0.85, OCT4=1, and SOX2=0.88. To obtain equal molarity of each factor 132 μl of KLF4, 58 μl of LIN28, 126 μl of c-MYC, 85 μl of NANOG, 100 μl of OCT4 and 88 μl of SOX2 mRNA (each at 100 ng/μl) would be added together. A 600 μg total dose for transfections would mean that 100 ng (using molarity conversions above) of each of six reprogramming mRNAs was used. Trans-IT mRNA transfection reagent was used to transfect these mRNA doses. For all transfections, mRNA pools were added to 250 μl of either DMEM/F12 media without additives or Advanced MEM media without additives. 5 μl of mRNA boost reagent and 5 μl of TransIT transfection reagent was added to each tube and incubated at room temp for two minutes before adding the transfection mix to 2.5 mls of either Advanced MEM media with 10% FBS+100 ng/ml of hFGFb or iPS media containing 100 ng/ml of hFGFb. Transfections were repeated everyday for 10-16 days. The media was changed 4 hours after each transfection. In some experiments, the cells were trypsinized and replated onto new MEF plates between 5-8 days after the inititial transfection. 1079 cells were split ⅙ or 1/12 onto new MEF plates while IMR90 cells were split ⅓ or ⅙ onto new MEF plates.

Reprogramming of Human Somatic Cells in MEF-Conditioned Medium.

1079 or IMR90 fibroblasts were plated at $3 \times 10^5$ cells per 10 cm dishes pre-coated with 0.1% gelatin (Millipore) and grown overnight. The 1079 or IMR90 fibroblasts were transfected with equal amounts of reprogramming factor mRNA (KLF4, LIN28, c-MYC, NANOG, OCT4, and SOX2) using TransIT mRNA transfection reagent (MirusBio, Madison, Wis.). For each transfection, either 6 μg, 18 μg, or 36 μg of each reprogramming mRNA (KLF4, LIN28, c-MYC, NANOG, OCT4, and SOX2) was used per 10-cm dish. A total of three transfections were performed, with one transfection being performed every other day with the medium being changed the day after each of the first and second transfections. All transfections were performed in MEF-conditioned medium. The day after the third transfection, the cells were trypsinized and $3 \times 10^5$ cells were plated on new 10-cm dishes pre-coated with 0.1% gelatin (Millipore). The cells were grown in MEF-conditioned medium for the duration of the experiment.

Similar daily mRNA transfections were also performed as described in the previous section with the only difference being that MEFs were not used as feeder layers, only MEF conditioned media was used.

Immunoflourescence.

The 1079 cells or 1079-derived iPS cell plates were washed with PBS and fixed in 4% paraformaldehyde in PBS for 30 minutes at room temperature. The iPS cells were then washed 3 times for 5 minutes each wash with PBS followed by three washes in PBS+0.1% Triton X-100. The iPS cells were then blocked in blocking buffer (PBS+0.1% Triton, 2% FBS, and 1% BSA) for 1 hour at room temperature. The cells were then incubated for 2 hours at room temperature with the primary antibody (mouse anti-human OCT4 Cat# sc-5279, Santa Cruz Biotechnology, Santa Cruz, Calif.), (rabbit anti-human NANOG Cat #3580, rabbit anti-human KLF4 Cat #4038, mouse anti-human LIN28 Cat#5930, rabbit anti-human c-MYC Cat#5605, rabbit anti-human SOX2 Cat#3579, and mouse anti-TRA-1-60 all from Cell Signaling Technology, Beverly, Mass.) at a 1:500 dilution in blocking buffer. After washing 5 times in PBS+0.1% Triton X-100, the iPS cells were incubated for 2 hours with the anti-rabbit Alexa Fluor 488 antibody (Cat #4412, Cell Signaling Technology), anti-mouse FITC secondary (Cat# F5262, Sigma), or an anti-mouse Alexa Fluor 555 (Cat#4409, Cell Signaling Technology) at 1:1000 dilutions in blocking buffer. Images were taken on a Nikon TS100F inverted microscope (Nikon, Tokyo, Japan) with a 2-megapixel monochrome digital camera (Nikon) using NIS-elements software (Nikon).

Example 1

This example describes tests to determine if transfections with mRNA encoding KLF4, LIN28, c-MYC, NANOG, OCT4 and SOX2 resulted in expression and proper subcellular localization of each respective protein product in newborn fetal foreskin 1079 fibroblasts. The mRNAs used in the experiments were made with pseudouridine-5'-triphosphate substituting for uridine-5'-triphosphate (Kariko et al. 2008). The 1079 fibroblasts were transfected with 4 μg of each mRNA per well of a 6-well dish and immunofluorescence analysis was performed 24 hours post-transfection. Endogenous KLF4, LIN28, NANOG, OCT4 and SOX2 protein levels were undetectable by immunoflourescence in untransfected 1079 cells (FIG. 1B, F, N, R, V). Endogenous levels of c-MYC were relatively high in untransfected 1079 cells (FIG. 1J). Transfections with mRNAs encoding the transcription factors, KLF4, c-MYC, NANOG, OCT4, and SOX2 all resulted in primarily nuclear localization of each protein 24 hours after mRNA transfections (FIG. 1D, L, P, T, X). The cytoplasmic mRNA binding protein, LIN28, was localized to the cytoplasm (FIG. 1H).

Example 2

Figure 2:
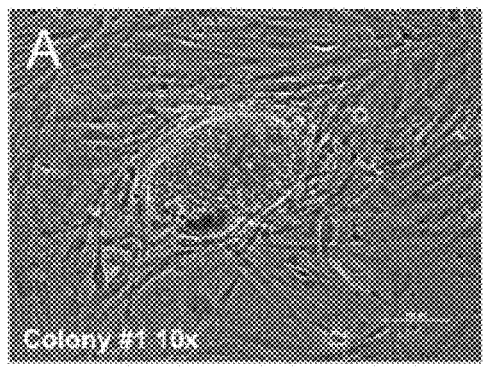
FIG. 2 shows that mRNA encoding human reprogramming factors (KLF4, LIN28, c-MYC, NANOG, OCT4, and SOX2) produce iPS cells in human somatic cells.
Figure 2:
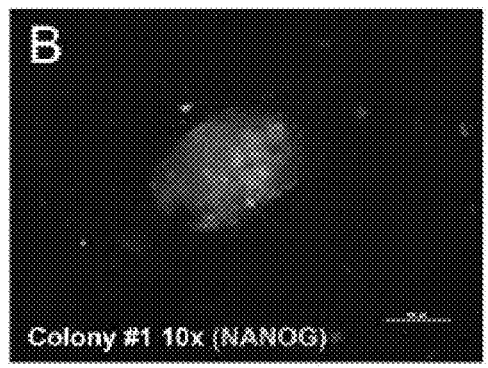
Figure 2:
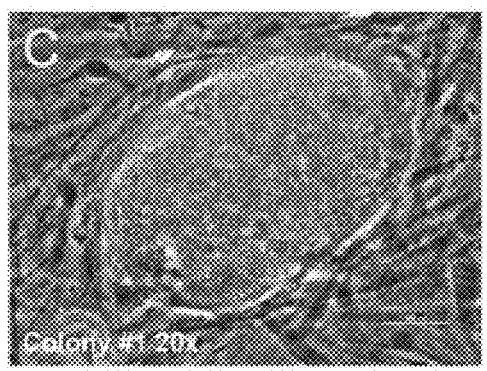
Figure 2:
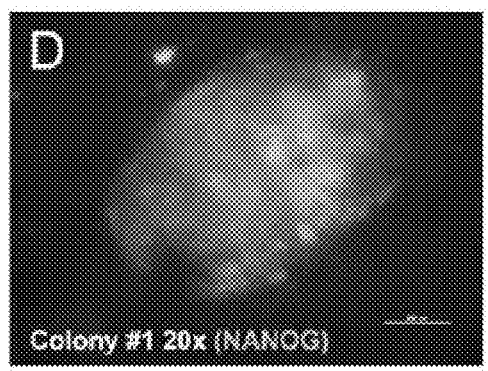

Having demonstrated efficient mRNA transfection and proper subcellular localization of the reprogramming proteins, this example describes development of a protocol for iPS cell generation from somatic fibroblasts. Equal amounts (by weight) of KLF4, LIN28, c-MYC, NANOG, OCT4, and SOX2 mRNAs were transfected into 1079 fibroblasts three times (once every other day). The day after the third transfection, the cells were plated onto irradiated MEF feeder cells and grown in iPS cell medium. Six days after plating the 1079 fibroblasts onto irradiated MEFs, two putative iPS cell colonies became apparent on the 10-cm plate transfected with 3 μg of each reprogramming factor mRNA (KLF4, LIN28, c-MYC, NANOG, OCT4, and SOX2). The colonies were allowed to grow until 12 days after the last transfection before they were fixed for immunofluorescence analysis. The inner cell mass-specific marker NANOG is often used to assay whether iPS cell colonies are truly iPS colonies (Gonzalez et al. 2009, Huangfu et al. 2008). NANOG expression arising from the mRNAs that were transfected 12 days earlier would be negligible based on previous reports on the duration of mRNA stability and expression (Kariko et al. 2008). Staining for NANOG showed that both of the two iPS cell colonies were NANOG positive (FIG. 2 B, D, and not shown). The surrounding fibroblasts that were not part of the iPS cell colony were NANOG negative, suggesting that they were not reprogrammed into iPS cells.

Figure 3:
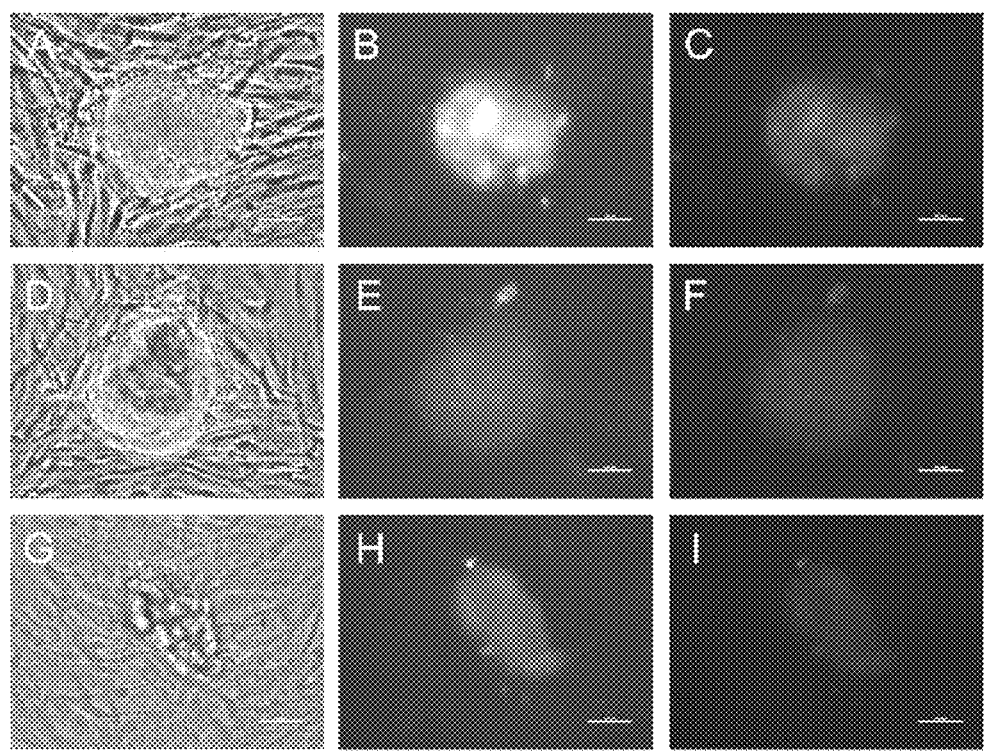
FIG. 3 shows that iPS colonies derived from human 1079 and IMR90 somatic cells are positive for NANOG and TRA-1-60.

In a subsequent experiment using the same protocol, both 1079 fibroblasts and human IMR90 fibroblasts were transfected with the same reprogramming mRNAs. Multiple colonies were detected as early as 4 days after plating the transfected cells on irradiated MEFs. When 6 µg of each mRNA (KLF4, LIN28, c-MYC, NANOG, OCT4, and SOX2) were used in transfections in 6-well dishes, 3 putative iPS cell colonies were later detected in both cell lines after plating on MEFs in 10-cm plates (FIG. 3). In addition to analyzing these colonies for expression of NANOG, TRA-1-60, a more stringent marker of fully reprogrammed iPS cells (Chan et al. 2009), was also used for immunofluorescence analysis. iPS colonies generated from 1079 fibroblasts (FIG. 3 A-F) and from IMR90 fibroblasts (FIG. 3 G-I) were positive for both NANOG and TRA-1-60, indicating that these colonies are fully reprogrammed type III iPS cell colonies. This protocol comprising three transfections of mRNAs encoding all six reprogramming factors and then plating onto MEF feeder cells resulted in a similar reprogramming efficiency (3-6 iPS colonies per $1\times10^6$ input cells) as was previously reported by protocols comprising delivery of the same reprogramming factors by transfection of an expression plasmid (Aoi et al. 2008).

Example 3

Figure 4:
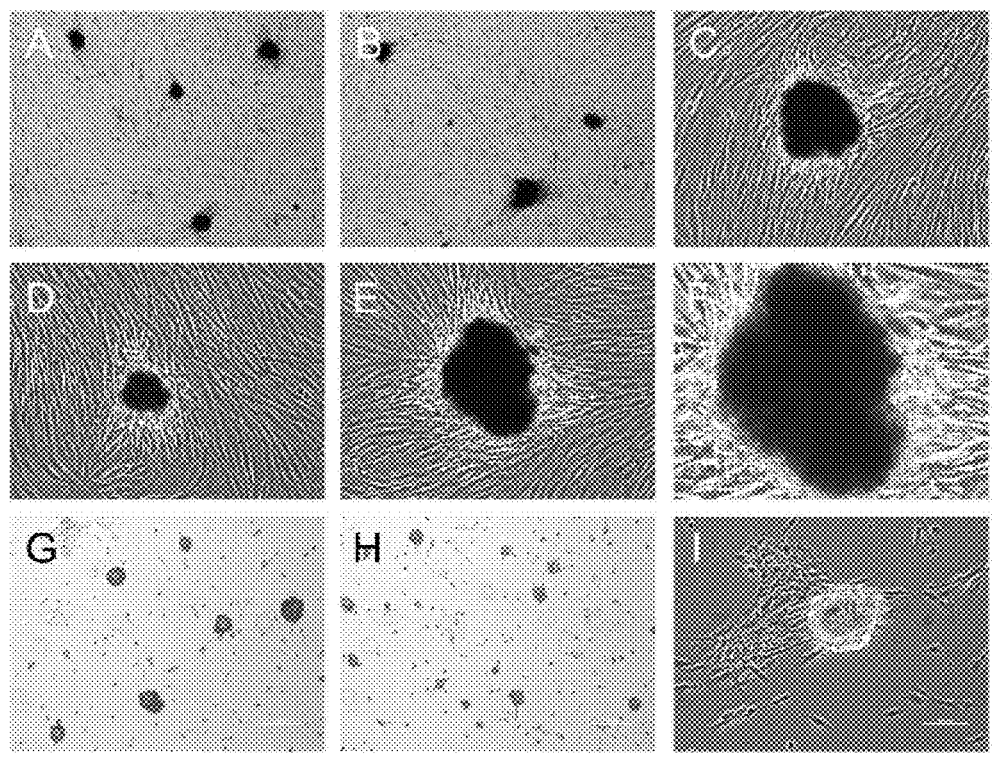
FIG. 4 shows that rapid, enhanced-efficiency iPSC colony formation is achieved by transfecting cells with mRNA encoding reprogramming factors in MEF-conditioned medium. Over 200 colonies were detected 3 days after the final transfection, in the 10-cm dish transfected three times with 36 μg of each reprogramming mRNA (i.e., encoding KLF4, LIN28, c-MYC, NANOG, OCT4, and SOX2). Representative iPSC colonies are shown at 4× (A, B), 10× (C-E) and 20× magnification (F). Eight days after the final mRNA transfection with mRNAs encoding the six reprogramming factors, greater than 1000 iPSC colonies were counted in IMR90 cells transfected with 18 μg (G, I) or 36 μg (H) of each of the six mRNAs. Representative colonies are shown at 4× magnification (G-H) and at 10× magnification (I).
Figure 5:
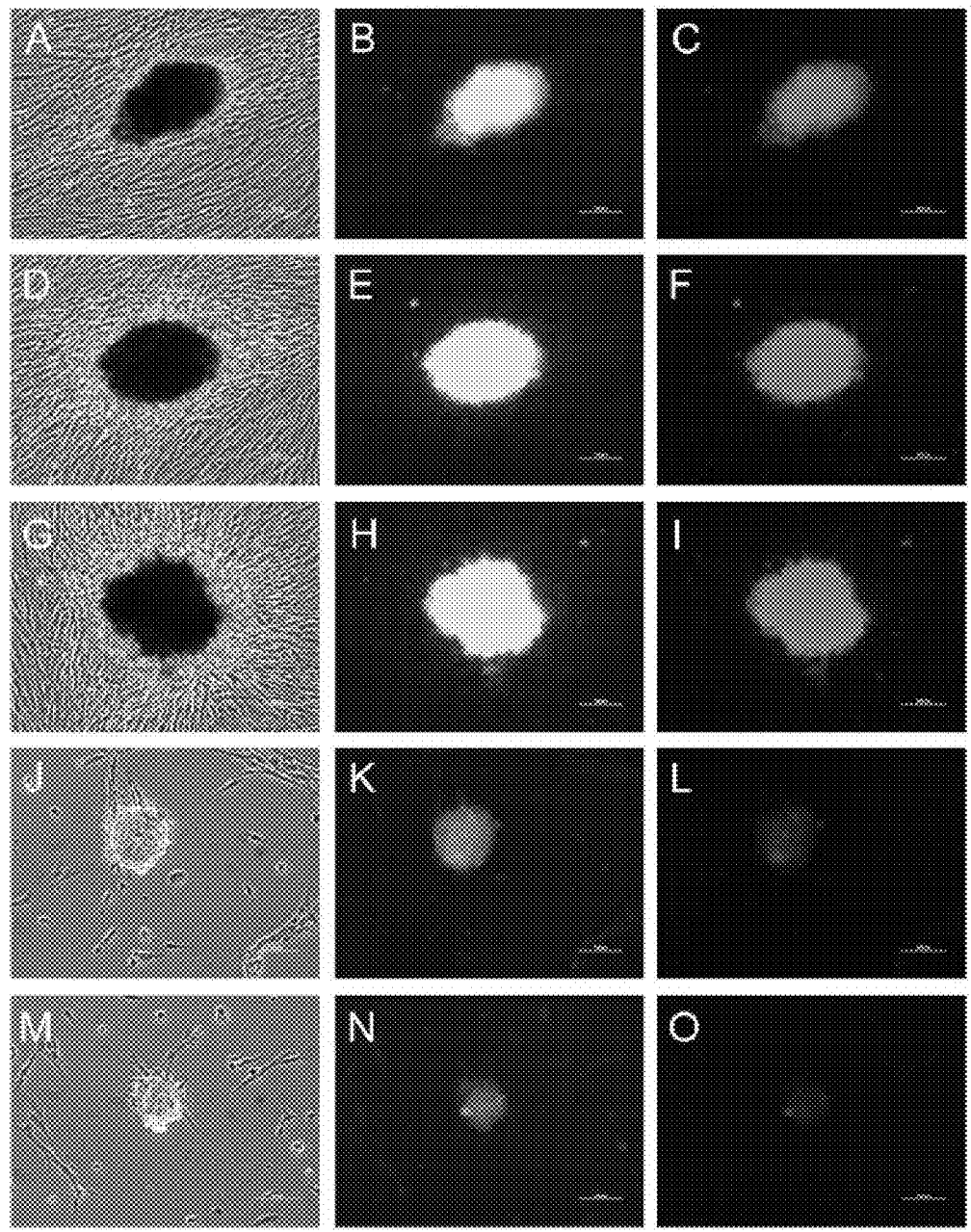
FIG. 5 shows that 1079- and IMR90-derived iPSC colonies are positive for both NANOG and TRA-1-60 expression. Eight days after the final mRNA transfection with 36 μg of mRNA for each of the six reprogramming factors, the 1079-derived iPSC colonies (shown in A, D, and G) are positive for NANOG (B, E, and H) and TRA-1-60 (C, F, and I). Eight days after the final mRNA transfection with 18 μg (J-L) or 36 μg (M-O) of mRNA for each of the six reprogramming factors, IMR90-derived iPS colonies are also positive for NANOG (K, N) and TRA-1-60 (L, O).

This example describes attempts to improve the efficiency of reprogramming differentiated cells using mRNA. In one approach, a protocol was used that comprised transfecting 1079 or IMR90 fibroblasts three times (once every other day) with the mRNAs encoding the six reprogramming factors in MEF-conditioned medium rather than in fibroblast medium and then growing the treated 1079 fibroblasts in MEF-conditioned medium rather than plating them on a MEF feeder layer after the treatments. At the highest transfection dose utilized (36 µg of each reprogramming factor per 10-cm dish), 208 iPS cell colonies were detected three days after the final transfection (FIG. A-F). Interestingly no iPS cell colonies were detected in the dishes transfected with either 6 or 18 µg of each of the reprogramming factors at the 3-day timepoint, suggesting that a dose above 18 µg was important, under these conditions, for iPS cell colony formation to occur within 3 days in MEF-conditioned medium. IMR90 cells showed an even higher number of iPS cell colonies, with around 200 colonies 8 days after the last transfection in the plate transfected with three 6-µg doses of each of the six reprogramming factor mRNAs and >1000 colonies in IMR90 cells transfected three times with 18-µg or 36-µg doses of each of the six reprogramming mRNAs (FIG. 4 G-I). Colonies were visible 3 days after the final transfection in 1079 cells, whereas colonies only became visible 6-7 days after the final transfection in IMR90 cells. Therefore, the more mature colonies derived from the 1079 cells were larger and denser and were darker in brightfield images compared to the IMR90 colonies (FIG. 4). All of the colonies on the 1079 plate transfected three times with 36 µg of each reprogramming mRNA were positive for both NANOG and TRA-1-60 8 days after the final mRNA transfection (FIG. 5 A-I). All of the more immature IMR90 iPS colonies were also positive for both NANOG and TRA-1-60 (FIG. 5 J-O), but showed less robust staining for both markers due to their less dense cellular nature compared to the more mature 1079 colonies (FIG. 5 A-I). The present protocol comprising delivery of the mRNAs into 1079 or IMR90 cells in MEF-conditioned medium had a reprogramming efficiency of 200 to >1000 colonies per $3\times10^5$ input cells. This protocol for inducing iPS cells was faster and almost 2-3 orders of magnitude more efficient than published protocols comprising transfecting fibroblasts with DNA plasmids encoding these same six reprogramming factors in fibroblast medium (Aoi et al. 2008). Still further, this protocol was over 7-40 times more efficient than the published protocol comprising delivery of reprogramming factors with lentiviruses, based on the published data that lentiviral delivery of reprogramming factors into 1079 newborn fibroblasts, which resulted in approximately 57 iPS cell colonies per $6\times10^5$ input cells (Aoi et al. 2008). This protocol is also much faster than the published methods.

REFERENCES

Aoi T, Yae K, Nakagawa M, Ichisaka T, Okita K, Takahashi K, Chiba T, Yamanaka S. 2008. Generation of pluripotent stem cells from adult mouse liver and stomach cells. Science 321: 699-702.

Banerjee A K. 1980. 5'-terminal cap structure in eucaryotic messenger ribonucleic acids. Microbiol. Rev 44: 175-205.

Chan E M, et al. 2009. Live cell imaging distinguishes bona fide human iPS cells from partially reprogrammed cells. Nat Biotechnol 27: 1033-1037.

Ebert A D, Yu J, Rose F F, Jr., Mattis V B, Lorson C L, Thomson J A, Svendsen C N. 2009. Induced pluripotent stem cells from a spinal muscular atrophy patient. Nature 457: 277-280.

Edmonds M. 1990. Polyadenylate polymerases. Methods Enzymol 181: 161-170.

Gershon P D. 2000. (A)-tail of two polymerase structures. Nat Struct Biol 7: 819-821.

Gonzalez F, Barragan Monasterio M, Tiscornia G, Montserrat Pulido N, Vassena R, Batlle Morera L, Rodriguez Piza I, Izpisua Belmonte J C. 2009. Generation of mouse-induced pluripotent stem cells by transient expression of a single nonviral polycistronic vector. Proc Natl Acad Sci USA 106: 8918-8922.

Graf T, Enver T. 2009. Forcing cells to change lineages. Nature 462: 587-594. Grudzien E, Stepinski J, Jankowska-Anyszka M, Stolarski R, Darzynkiewicz E, Rhoads R E. 2004. Novel cap analogs for in vitro synthesis of mRNAs with high translational efficiency. RNA 10: 1479-1487.

Grudzien-Nogalska E, Jemielty J, Kowalska J, Darzynkiewicz E, Rhoads R. 2007. Phosphorothioate cap analogs stabilize mRNA and increase translational efficiency in mammalian cells. RNA 13: 1745-1755.

Higman M A, Bourgeois N, Niles E G. 1992. The vaccinia virus mRNA (guanine-N7-)-methyltransferase requires both subunits of the mRNA capping enzyme for activity. J Biol Chem 267: 16430-16437.

Higman M A, Christen L A, Niles E G. 1994. The mRNA (guanine-7-)methyltransferase domain of the vaccinia virus mRNA capping enzyme. Expression in *Escherichia* coli and structural and kinetic comparison to the intact capping enzyme. J Biol Chem 269: 14974-14981.

Huangfu D, Osafune K, Maehr R, Guo W, Eijkelenboom A, Chen S, Muhlestein W, Melton D A. 2008. Induction of pluripotent stem cells from primary human fibroblasts with only Oct4 and Sox2. Nat Biotechnol 26: 1269-1275.

Jemielity J, Fowler T, Zuberek J, Stepinski J, Lewdorowicz M, Niedzwiecka A, Stolarski R, Darzynkiewicz E, Rhoads R E. 2003. Novel "anti-reverse" cap analogs with superior translational properties. RNA 9: 1108-1122.

Kariko K, Muramatsu H, Welsh F A, Ludwig J, Kato H, Akira S, Weissman D. 2008. Incorporation of pseudouridine into mRNA yields superior nonimmunogenic vector with increased translational capacity and biological stability. Mol Ther 16: 1833-1840.

Lee G, et al. 2009. Modelling pathogenesis and treatment of familial dysautonomia using patient-specific iPSCs. Nature 461: 402-406.

Mackie G A. 1988. Vectors for the synthesis of specific RNAs in vitro. Biotechnology 10: 253-267.

Maehr R, Chen S, Snitow M, Ludwig T, Yagasaki L, Goland R, Leibel R L, Melton D A. 2009. Generation of pluripotent stem cells from patients with type 1 diabetes. Proc Natl Acad Sci USA 106: 15768-15773.

Martin S A, Paoletti E, Moss B. 1975. Purification of mRNA guanylyltransferase and mRNA (guanine-7-) methyltransferase from vaccinia virions. J Biol Chem 250: 9322-9329.

Myette J R, Niles E G. 1996. Domain structure of the vaccinia virus mRNA capping enzyme. Expression in *Escherichia coli* of a subdomain possessing the RNA 5'-triphosphatase and guanylyltransferase activities and a kinetic comparison to the full-size enzyme. J Biol Chem 271: 11936-11944.

Nakagawa M, Koyanagi M, Tanabe K, Takahashi K, Ichisaka T, Aoi T, Okita K, Mochiduki Y, Takizawa N, Yamanaka S. 2008. Generation of induced pluripotent stem cells without Myc from mouse and human fibroblasts. Nat Biotechnol 26: 101-106.

Okita K, Nakagawa M, Hyenjong H, Ichisaka T, Yamanaka S. 2008. Generation of mouse induced pluripotent stem cells without viral vectors. Science 322: 949-953.

Ozawa T, Kishi H, Muraguchi A. 2006. Amplification and analysis of cDNA generated from a single cell by 5'-RACE: application to isolation of antibody heavy and light chain variable gene sequences from single B cells. Biotechniques 40: 469-470, 472, 474 passim.

Peng Z H, Sharma V, Singleton S F, Gershon P D. 2002. Synthesis and application of a chain-terminating dinucleotide mRNA cap analog. Org Lett 4: 161-164.

Shuman S. 1995. Capping enzyme in eukaryotic mRNA synthesis. Prog Nucleic Acid Res Mol Biol 50: 101-129.

Shuman. 2001. Structure, mechanism, and evolution of the mRNA capping apparatus. Prog Nucleic Acid Res Mol Biol 66: 1-40.

Shuman S, Surks M, Furneaux H, Hurwitz J. 1980. Purification and characterization of a GTP-pyrophosphate exchange activity from vaccinia virions. Association of the GTP-pyrophosphate exchange activity with vaccinia mRNA guanylyltransferase. RNA (guanine-7-)methyltransferase complex (capping enzyme). J Biol Chem 255: 11588-11598.

Stadtfeld M, Nagaya M, Utikal J, Weir G, Hochedlinger K. 2008. Induced pluripotent stem cells generated without viral integration. Science 322: 945-949.

Stepinski J, Waddell C, Stolarski R, Darzynkiewicz E, Rhoads R E. 2001. Synthesis and properties of mRNAs containing the novel "anti-reverse" cap analogs 7-methyl (3'-O-methyl)GpppG and 7-methyl (3'-deoxy)GpppG. RNA 7: 1486-1495.

Studier F W, Moffatt B A. 1986. Use of bacteriophage T7 RNA polymerase to direct selective high-level expression of cloned genes. J Mol Biol 189: 113-130.

Takahashi K, Yamanaka S. 2006. Induction of pluripotent stem cells from mouse embryonic and adult fibroblast cultures by defined factors. Cell 126: 663-676.

Takahashi K, Tanabe K, Ohnuki M, Narita M, Ichisaka T, Tomoda K, Yamanaka S. 2007. Induction of pluripotent stem cells from adult human fibroblasts by defined factors. Cell 131: 861-872.

Wang S P, Deng L, Ho C K, Shuman S. 1997. Phylogeny of mRNA capping enzymes. Proc Natl Acad Sci USA 94: 9573-9578.

Wilusz J, Shenk T. 1988. A 64 kd nuclear protein binds to RNA segments that include the AAUAAA polyadenylation motif. Cell 52: 221-228.

Woltjen K, et al. 2009. piggyBac transposition reprograms fibroblasts to induced pluripotent stem cells. Nature 458: 766-770.

Xu C, Inokuma M S, Denham J, Golds K, Kundu P, Gold J D, Carpenter M K. 2001. Feeder-free growth of undifferentiated human embryonic stem cells. Nat Biotechnol 19: 971-974.

Yu J, Hu K, Smuga-Otto K, Tian S, Stewart R, Slukvin, I I, Thomson J A. 2009. Human induced pluripotent stem cells free of vector and transgene sequences. Science 324: 797-801.

Yu J, et al. 2007. Induced pluripotent stem cell lines derived from human somatic cells. Science 318: 1917-1920.

Zhou H, et al. 2009. Generation of induced pluripotent stem cells using recombinant proteins. Cell Stem Cell 4: 381-384.

We claim:

1. A method for changing the state of differentiation of a somatic cell comprising:
   introducing in vitro-synthesized mRNA molecules encoding one or more iPS cell induction factors into a somatic cell to generate a reprogrammed cell,
   wherein said mRNA molecules (a) have been treated with RNase III, (b) are polyadenylated, and (c) comprise a population of mRNA molecules, of which greater than 80% are capped.

2. The method of claim 1, wherein said introducing comprises delivering said mRNA to said somatic cell with a transfection reagent.

3. The method of claim 1, wherein said reprogrammed cell is a dedifferentiated cell.

4. The method of claim 1, wherein said reprogrammed cell is a transdifferentiated cell.

5. The method of claim 1, wherein said mRNA molecules comprise a poly-A tail that is 50-200 nucleotides in length.

6. The method of claim 1, wherein said mRNA molecules comprise a poly-A tail that is 100-200 nucleotides in length.

7. The method of claim 1, wherein said mRNA molecules have a cap with a cap1 structure, wherein the penultimate nucleotide with respect to the cap nucleotide has a methyl group on the 2'-position of the ribose.

8. The method of claim 1, wherein greater than 99% of said mRNA molecules are capped.

9. The method of claim 1, wherein said mRNA comprises pseudouridine in place of uridine.

10. The method of claim 1, wherein said iPS cell induction factor is selected from the group consisting of KLF4, LIN28, c-MYC, NANOG, OCT4, and SOX2.

11. The method of claim 1, wherein said introducing comprises introducing mRNA molecules encoding a plurality of iPS cell induction factors into said somatic cell.

12. The method of claim 11, wherein said plurality of iPS cell induction factors comprises each of KLF4, LIN28, c-MYC, NANOG, OCT4, and SOX2.

13. The method of claim 1, wherein said somatic cell is a fibroblast.

14. The method of claim 1, wherein said reprogrammed cell is a pluripotent stem cell.

15. The method of claim 1, wherein said dedifferentiated cell expresses NANOG and TRA-1-60.

16. The method of claim 1, wherein said somatic cell is in vitro.

17. The method of claim 1, wherein said somatic cell resides in culture.

18. The method of claim 17, wherein said cells reside in MEF-conditioned medium.

19. The method of claim 1, wherein said mRNA molecules are purified to remove RNase III digestion products prior to said introducing.

20. The method of claim 1, wherein said mRNA molecules comprise *Xenopus laevis* B-globin 5' and 3' untranslated regions.

21. The method of claim 1, wherein said mRNA molecules comprise a Kozak consensus sequence.

22. The method of claim 11, wherein said plurality of iPS cell induction factors comprises each of OCT4, SOX2, KLF4, and a MYC family protein.

23. The method of claim 22, wherein the MYC family protein is selected from the group consisting of c-MYC, L-MYC, and N-MYC.

24. The method of claim 22, further comprising at least one iPS cell induction factor selected from among LIN28 and NANOG.

25. The method of claim 1, wherein the in vitro-synthesized mRNA molecules are synthesized by amplification of mRNA molecules derived from one or more cells using an RNA amplification reaction method that results in synthesis of sense RNA.

26. The method of claim 1, further comprising repeating said introducing daily for 10-16 days.

* * * * *